(12) United States Patent
Boulle et al.

(10) Patent No.: US 7,294,641 B2
(45) Date of Patent: Nov. 13, 2007

(54) HETEROCYCLIC COMPOUND FOR STIMULATING OR INDUCING THE GROWTH OF THE HAIR OR EYELASHES AND/OR SLOWING DOWN THEIR LOSS, COMPOSITION COMPRISING IT AND ITS USES

(75) Inventors: Christophe Boulle, Lagny S/Marne (FR); Roger Rozot, Lagny S/Marne (FR); Maria Dalko, Gif S/Yvette (FR)

(73) Assignee: L'Oreal, Paris (FR)

( * ) Notice: Subject to any disclaimer, the term of this patent is extended or adjusted under 35 U.S.C. 154(b) by 385 days.

(21) Appl. No.: 10/671,508

(22) Filed: Sep. 29, 2003

(65) Prior Publication Data

US 2006/0008436 A1    Jan. 12, 2006

Related U.S. Application Data

(60) Provisional application No. 60/415,462, filed on Oct. 3, 2002.

(30) Foreign Application Priority Data

Sep. 27, 2002    (FR) .................................. 02 12018

(51) Int. Cl.
| | |
|---|---|
| *A61Q 7/00* | (2006.01) |
| *A61K 8/49* | (2006.01) |
| *A61K 31/4178* | (2006.01) |
| *A61K 31/422* | (2006.01) |
| *A61K 31/427* | (2006.01) |

(52) U.S. Cl. ...................... 514/366; 514/369; 514/376; 514/397; 514/461; 514/398; 424/70.1

(58) Field of Classification Search ................ 514/461, 514/366, 369, 376, 397
See application file for complete search history.

(56) References Cited

FOREIGN PATENT DOCUMENTS

| | | | |
|---|---|---|---|
| DE | 40 27 038 A1 | 3/1992 | |
| JP | 11-302280 A | 11/1999 | |
| WO | WO98/53790 A2 | 12/1998 | |
| WO | WO 00/10573 A1 | 3/2000 | |
| WO | WO 01/62237 A2 | 8/2001 | |
| WO | WO 02/26706 A2 | 4/2002 | |
| WO | WO 02/074752 A1 | 9/2002 | |

OTHER PUBLICATIONS

Shinji, Patent Abstracts of Japan, "Thiazolidine Derivative, and Medicine Containing the Same as Active Ingredient", Publication No. 11302280, Publication Date—Nov. 2, 1999, vol. 2000, No. 2.
Saakaa, Patent Abstracts of Japan, "Condensed Pyrrole Derivatives, and Medicines Containing the Derivatives as Active Ingredients", Publication No. 09249669, Publication Date—Sep. 22, 1997, vol. 1998, No. 1.
Abstract XP002241668, Chemical Abstracts Service, Database Accession No. 136;95580, Columbus, Ohio, 2001.
French Search Report Corresponding to FR 02/12018, Issued on May 20, 2003—4 Pages.

*Primary Examiner*—Laura L. Stockton
(74) *Attorney, Agent, or Firm*—Buchanan, Ingersoll & Rooney, PC

(57) ABSTRACT

Heterocyclic compounds useful for stimulating/inducing the growth of keratinous fibers, notably human hair/eyelashes, and/or slowing the loss of same, have the following structural formula (I) or salt thereof:

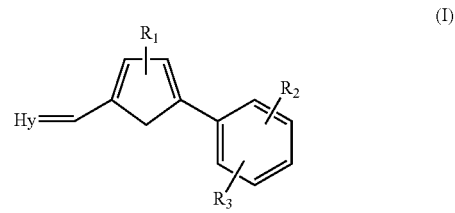

in which Hy is a heterocycle of 4 to 7 atoms, optionally comprising carbonyl/thiocarbonyl functional groups, and G is O, S or NH.

67 Claims, No Drawings

HETEROCYCLIC COMPOUND FOR STIMULATING OR INDUCING THE GROWTH OF THE HAIR OR EYELASHES AND/OR SLOWING DOWN THEIR LOSS, COMPOSITION COMPRISING IT AND ITS USES

This application claims priority under 35 U.S.C. § 119 of FR 02/12018, filed Sep. 27, 2002, and of provisional application Ser. No. 60/415,462, filed Oct. 3, 2002, both hereby expressly incorporated by reference. This application is also a continuation of said '462 provisional.

FIELD OF THE INVENTION

A subject-matter of the invention is the use of an effective amount of a heterocyclic compound and more especially of a phenylfuran, of a phenylthiophene or of a phenylpyrrole in a composition intended to induce and/or stimulate the growth of keratinous fibres, in particular human keratinous fibres, and/or to slow down their loss. Another subject-matter of the invention is such a composition. It additionally relates to a cosmetic treatment process and to novel heterocyclic compounds intended to stimulate the growth of keratinous fibres and/or to slow down their loss.

The human keratinous fibres to which the invention applies are in particular the hair, eyebrows, eyelashes, beard hairs, moustache hairs and pubic hairs. More especially, the invention applies to human hair and/or eyelashes.

In particular, the invention relates to a composition for caring for or making up the hair or eyelashes, comprising an effective amount of a heterocyclic compound possessing a phenyl radical, intended to increase their density and/or to improve their appearance.

BACKGROUND OF THE INVENTION

The growth of the hair and its renewal are mainly determined by the activity of the hair follicles and of their matrix environment. Their activity is cyclical and essentially comprises three phases, namely the anagen phase, the catagen phase and the telogen phase.

The anagen phase (active or growth phase), which lasts several years and during which the hair lengthens, is succeeded by a very short and transitory catagen phase, which lasts a few weeks. During this phase, the hair undergoes a change, the follicle atrophies and its implantation in the skin appears less and less deep.

The terminal phase or telogen phase, which lasts several months, corresponds to a resting phase of the follicle and the hair finishes by falling out. At the end of this resting period, a new follicle is regenerated there and another cycle recommences.

The hair is therefore continuously renewed and, of the approximately 150 000 individual hairs which make up the hair, approximately 10% are at rest and will be replaced in a few months.

The natural loss of the hair can be estimated, on average, at a few hundred hairs per day for a normal physiological state. This constant physical renewal process undergoes a natural change during the course of ageing; the hairs become finer and their cycles shorter.

In addition, various causes can result in a significant, temporary or definitive, hair loss. The hair can be lost or detrimentally affected during recovery from pregnancy (post partum), during conditions of undernourishment or of dietary imbalances or during conditions of asthenia or of hormonal dysfunctioning, as may be the case during the course of or during recovery from the menopause. Hair can also be lost or detrimentally affected in connection with seasonal phenomena.

It may also be a matter of alopecia, which is essentially due to a disturbance of hair renewal which results, first, in an acceleration in the frequency of the cycles to the detriment of the quality of the hair and then of its amount. The successive growth cycles result in hair which is increasingly fine and increasingly short, which is gradually converted to an unpigmented down and which thus results in a gradual thinning of the head of hair. Areas are preferentially affected, in particular the temples or the front of the head in men, and, in women, a diffuse alopecia of the vertex is observed.

The term "alopecia" also covers a whole family of conditions of the hair follicle having, as a final consequence, partial or general permanent hair loss. It is a matter more particularly of androgenic alopecia. In a significant number of cases, early hair loss takes place in genetically predisposed subjects; it is then a matter of androchronogenetic alopecia. This form of alopecia affects men in particular.

Furthermore, it is known that certain factors, such as hormonal imbalance, physiological stress or malnutrition, can accentuate the phenomenon.

In some dermatosis conditions of the scalp with an inflammatory nature, such as, for example, psoriasis or seborrhoeic dermatitis, hair loss can be greatly increased or can result in highly disrupted cycles of the follicles.

There has been a search for many years, in the cosmetic or pharmaceutical industry, for compositions which make it possible to eliminate or reduce alopecia and in particular to induce or stimulate hair growth or to decrease hair loss.

From this viewpoint, a large number of compositions comprising very diverse active principles, such as, for example, 2,4-diamino-6-piperidinopyrimidine 3-oxide or "minoxidil", disclosed in U.S. Pat. No. 4,139,619 and U.S. Pat. No. 4,596,812, or its numerous derivatives, such as those disclosed, for example, in Patent Applications EP 0 353 123, EP 0 356 271, EP 0 408 442, EP 0 522 964, EP 0 420 707, EP 0 459 890 and EP 0 519 819, have already been provided.

Clinical studies have demonstrated that $PGF_{2\alpha}$ analogues have the property of bringing about the growth of body hairs and eyelashes in man and animals (Murray A. and Johnstone M. D., 1997, Am. J. Opht., 124(4), 544-547). In man, tests carried out on the scalp have shown that a prostaglandin $E_2$ analogue (viprostol) has the property of increasing hair density (Roenig H H., 1988, Clinic Dermatol., 6(4), 119-121).

Furthermore, Patent WO 98/33497 discloses pharmaceutical compositions comprising prostaglandins or prostaglandin derivatives intended to combat hair loss in man. Prostaglandins of the $A_2$, $F_{2\alpha}$ and $E_2$ type are mentioned as preferred.

However, prostaglandins are molecules with a very short biological half-life which act autocrinally or paracrinally, this reflecting the local and labile nature of the metabolism of prostaglandins (Narumiya S. et al., 1999, Physiol. Rev., 79(4), 1193-1226).

It thus appears important, to maintain and/or increase hair density in man, to retain the endogenous reserves of $PGF_{2\alpha}$ and of $PGE_2$ in the various compartments of the hair follicle or of its immediate cutaneous environment.

A solution which gives good results is the use of compounds which are inhibitors of lipoxygenase and/or inducers of cyclooxygenase for the purpose of promoting hair growth; one hypothesis is that the use of such compounds directs the metabolism of the fatty acids towards the endogenous synthesis of prostaglandins in preference to other routes.

However, to further improve the results, it would be desirable to be able to prolong the activity of the prostaglandins involved in the growth and the preservation of the individual living hair.

Furthermore, it is well known that the programmes of differentiation of the keratinocytes of the epidermis and of the hair follicle are clearly different. Thus, it is known that the keratins of the hair shaft represents a family (Langbein et al., 2001, J. Biol. Chem., 276, 35123-35132) distinct from that expressed in the epidermis, that differentiation markers such as keratins $K_1$ and $K_{10}$ are not expressed in the hair follicle and in particular in the outer sheath (Lenoir et al., 1988, Dev. Biol., 130, 610-620), that trichohyalin (O'Guin et al., 1992, J. Invest. Dermatol., 98, 24-32) and keratin K6irs (Porter et al., 2001, Br. J. Dermatol., 145, 558-568) are expressed in the hair follicle, in particular in the inner sheath, but not in the epidermis, and that cyclooxygenase type 1, while it is expressed in the epidermis, is not expressed in the keratinocytes of the hair follicle but in the dermal papilla (Michelet et al., 1997, J. Invest. Dermatol., 108, 205-209).

The Applicant has now demonstrated that an enzyme specifically involved in the decomposition of these prostaglandins is present in the dermal papilla of the individual hair, which is a determining compartment for the life of the individual hair. This is because the Applicant has now proved the presence of 15-hydroxyprostaglandin dehydrogenase (abbreviated to 15-PGDH) therein. In addition, it has shown that the inhibition of 15-PGDH has a beneficial effect on hair growth.

This is why the present invention relates to a composition for the care or treatment of human keratinous fibres and in particular hair fibres comprising at least one specific inhibitor of 15-hydroxyprostaglandin dehydrogenase and a physiologically acceptable medium.

15-PGDH is a key enzyme in the deactivation of prostaglandins, in particular of $PGF_{2\alpha}$ and of $PGE_2$, which are important mediators of the growth and survival of the individual hair. It corresponds to the EC 1.1.1.141 classification and is NAD+-dependent. It has been isolated from pig kidney; its inhibition by a thyroid hormone, triiodothyronine, at doses much greater than physiological doses has in particular been observed.

However, provision had never been made to use a 15-PGDH inhibitor for maintaining and/or increasing the density of human keratinous fibres and in particular hair density and/or for reducing the heterogeneity in the diameters of keratinous fibres and in particular of head hairs in man. Increasing the density of keratinous fibres and in particular hair density is understood to mean increasing the number of keratinous fibres and in particular of head hairs per $cm^2$ of skin or scalp.

ACCOUNT OF THE INVENTION

The Applicant has found that some heterocyclic compounds and in particular some phenylfurans, phenylthiophenes or phenylpyrroles, which may or may not be salified, surprisingly possess a favourable activity in improving the density of human keratinous fibres, in particular hair fibres. Moreover, it has been found that these compounds are inhibitors of 15-hydroxyprostaglandin dehydrogenase.

A subject-matter of the present invention is thus the use, in particular the cosmetic use, of at least one heterocyclic compound of formula (I) or of one of its salts,

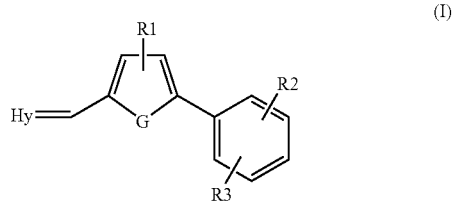

in which:

Hy represents a heterocycle with 4, 5, 6 or 7 atoms optionally comprising at least one carbonyl functional group and/or one thiocarbonyl functional group, the said heterocycle optionally being substituted by at least one substituent chosen from a halogen, OR, SR, NRR', COR, CSR, NRCONR'R", C(=NR)R', C(=NR)NR'R", NRC(=NR')NR"R''', OCOR, COSR, SCOR, CSNRR', NRCSR', NRCSNR'R", COOR, CONRR', $CF_3$, CN, NRCOR', $SO_2R'$, $SO_2NRR'$ or $NRSO_2R'$ groups, saturated or unsaturated and linear or branched $C_1$-$C_{20}$ alkyl radicals or saturated or unsaturated rings of 4 to 7 atoms optionally comprising at least one heteroatom, it being possible for these rings to be separate or fused, it being possible for the alkyl radicals and the rings, in addition, to be substituted, where R, R', R" and R''', which are identical or different, denote a hydrogen, a linear or branched $C_1$-$C_{20}$ alkyl radical or an aryl radical which is optionally substituted;

G represents O, S or NH;

$R_1$, $R_2$ and $R_3$ represent, independently of one another, a hydrogen, a halogen, an $OR_0$, $SR_0$, $NR_0R_0'$, $COR_0$, $CSR_0$, $NR_0CONR_0'R_0"$, $C(=NR_0)R_0'$, $C(=NR_0)NR_0'R_0"$, $NR_0C(=NR_0')NR_0"R_0'''$, $OCOR_0$, $COSR_0$, $SCOR_0$, $CSNR_0R_0'$, $NR_0CSR_0'$, $NR_0CSNR_0'R_0"$, $COOR_0$, $CONR_0R_0'$, $CF_3$, $NO_2$, CN, $NR_0COR_0'$, $SO_2R_0'$, $SO_2NR_0R_0'$ or $NR_0SO_2R_0'$ group, a saturated or unsaturated and linear or branched $C_1$-$C_{20}$ alkyl radical or at least one saturated or unsaturated ring of 4 to 7 atoms optionally comprising at least one heteroatom, it being possible for the rings to be separate or fused, it being possible for the alkyl radicals and the rings, in addition, to be substituted, where $R_0$, $R_0'$, $R_0"$ and $R_0'''$, which are identical or different, denote a hydrogen, a linear or branched $C_1$-$C_{20}$ alkyl radical or an aryl radical which is optionally substituted;

as agent for inducing and/or stimulating the growth of keratinous fibres, in particular human keratinous fibres, such as the eyelashes and hair of human beings, and/or slowing down their loss and/or increasing their density.

The invention also applies to the keratinous fibres of non-human mammals (dogs, horses or cats, for example).

The invention also relates to the cosmetic use of at least one heterocycle of formula (I) or of one of its salts in a cosmetic composition for caring for and/or making up human keratinous fibres in order to induce and/or stimulate their growth, to slow down their loss and/or to increase their density and/or to treat androgenic alopecia and to the use of at least one compound of formula (I) or of one of its salts in the preparation of a composition for caring for or treating human keratinous fibres intended to induce and/or stimulate the growth of the fibres and/or to slow down their loss and/or to increase their density and/or to treat androgenic alopecia.

The human keratinous fibres to which the invention applies are in particular the hair, eyebrows, eyelashes, beard hairs, moustache hairs and pubic hairs. More especially, the invention applies to human hair and/or eyelashes.

The invention also relates to the cosmetic use of at least one heterocyclic compound of formula (I) or of one of its salts in a cosmetic composition for human hair care in order to reduce hair loss and/or to increase hair density. A further subject-matter of the invention is the use of at least one heterocyclic compound of formula (I) or of one of its salts in the preparation of a human hair composition intended to induce and/or stimulate the growth of the hair and/or to slow down hair loss and/or to increase hair density.

In particular, the invention relates to the cosmetic use of at least one heterocyclic compound of formula (I) or of one of its salts in a cosmetic composition for human hair care for treating alopecia of natural origin and in particular androchronogenetic alopecia or to the use of at least one heterocyclic compound of formula (I) or of one of its salts in the preparation of a human hair composition intended to treat alopecia of natural origin and in particular androgenic alopecia. Thus, this composition makes it possible to keep the hair in good condition and/or to combat natural hair loss and more especially that of men.

A further subject-matter of the invention is the cosmetic use of at least one heterocyclic compound of formula (I) or of one of its salts in a cosmetic composition for caring for and/or for making up human eyelashes for inducing and/or stimulating the growth of the eyelashes and/or increasing their density and the use of at least one heterocyclic compound of formula (I) or of one of its salts in the preparation of a composition for caring for and/or treating human eyelashes intended to induce and/or stimulate the growth of the eyelashes and/or to increase their density. This composition thus makes it possible to keep the eyelashes in good condition and/or to improve their condition and/or their appearance.

Another subject-matter of the invention is a composition for caring for and/or making up keratinous fibres, in particular human keratinous fibres, comprising a physiologically acceptable medium and at least one heterocyclic compound of formula (I) or one of its salts.

Another subject-matter of the invention is the use of at least one heterocyclic compound of formula (I) or of one of its salts as inhibitor of 15-hydroxyprostaglandin dehydrogenase of the human skin. Another subject-matter of the invention is the use of at least one heterocyclic compound of formula (I) or of one of its salts in the manufacture of a composition intended to treat disorders related to 15-hydroxyprostaglandin dehydrogenase, in particular in man.

Another subject-matter of the invention is a process for the cosmetic treatment of keratinous fibres (in particular hair or eyelashes) and/or of the skin from where the said fibres emerge, including the scalp and eyelids, intended in particular to stimulate the growth of human keratinous fibres and/or slow down their loss, characterized in that it consists in applying, to the keratinous fibres and/or the skin from where the said fibres emerge, a cosmetic composition comprising an effective amount of at least one compound of formula (I) or of one of its salts, in leaving this composition in contact with the keratinous fibres and/or the skin from where the said fibres emerge and optionally in rinsing the fibres and/or the said skin.

This treatment process exhibits the characteristics of a cosmetic process in so far as it makes it possible to improve the attractiveness of the keratinous fibres by giving them greater vigour and an improved appearance. In addition, it can be used daily for several months without a medical prescription.

More especially, a subject-matter of the present invention is a process for the cosmetic care of human hair and/or the human scalp for the purpose of improving their condition and/or their appearance, characterized in that it consists in applying, to the hair and/or the scalp, a cosmetic composition comprising an effective amount of at least one compound of formula (I) or one of its salts, in leaving this composition in contact with the hair and/or the scalp and optionally in rinsing the hair and/or the scalp.

Another subject-matter of the invention is a process for the cosmetic care of and/or for making up human eyelashes for the purpose of improving their condition and/or their appearance, characterized in that it consists in applying, to the eyelashes and/or eyelids, a mascara composition comprising at least one compound of formula (I) or one of its salts and in leaving this composition in contact with the eyelashes and/or eyelids. This mascara composition can be applied alone or as an undercoat of a conventional pigmented mascara and can be removed like a conventional pigmented mascara.

Another subject-matter of the invention is a composition for caring for or making up keratinous fibres comprising, in a physiologically acceptable medium, in particular a cosmetic medium, at least one compound of formula (I) or one of its salts and at least one additional active principle which promotes the regrowth of human keratinous fibres and/or which limits the loss chosen from aminexil, FP receptor agonists and vasodilators and chosen more especially from aminexil, minoxidil, latanoprost, butaprost and travoprost.

Another subject-matter of the invention is the cosmetic use of at least one heterocyclic compound of formula (I) or of one of its salts in a cosmetic composition as agent for preserving the amount and/or the activity of prostaglandins in the hair follicle.

Another subject-matter of the invention is the use of at least one heterocyclic compound of formula (I) or of one of its salts in the manufacture of a composition intended to preserve the amount and/or the activity of prostaglandins in the hair follicle.

DETAILED DESCRIPTION OF THE
EMBODIMENTS OF THE INVENTION

In the continuation of the text, and unless expressly mentioned, the use of the term "compound of formula (I)" should be understood as meaning both the compound of formula (I) in the neutral, acidic or basic form and in the form of salts.

The term "15-hydroxyprostaglandin dehydrogenase inhibitor" is understood to mean a compound of formula (I) which is capable of inhibiting or reducing the activity of the enzyme 15-PGDH, in particular in man, and/or is capable of inhibiting, reducing or slowing down the reaction catalysed by this enzyme.

According to an advantageous embodiment of the invention, the compound of formula (I) is a specific inhibitor of 15-PGDH; the term "specific inhibitor" is understood to mean an active principle which is not or only to a slight extent an inhibitor of the synthesis of prostaglandins, in particular of the synthesis of $PGF_{2\alpha}$ or $PGE_2$. According to a specific embodiment of the invention, the inhibitor of 15-PGDH is not or only to a slight extent an inhibitor of the synthesis of prostaglandins, in particular of the synthesis of $PGF_{2\alpha}$ or $PGE_2$. According to a specific embodiment of the invention, the inhibitor of 15-PGDH is not or only to a slight extent an inhibitor of prostaglandin synthase (PGF synthase).

This is because the Applicant has now found that PGF synthase is also expressed in the dermal papilla. The maintenance of an effective amount of prostaglandins at the site of action thus results from a complex biological equilibrium between the synthesis and the decomposition of these molecules. The exogenous contribution of compounds which inhibit catabolism will therefore be less effective if this activity is combined with inhibition of the synthesis of these prostaglandins.

The compounds of formula (I), which may or may not be salified, advantageously exhibit an inhibitory activity for 15-PGDH which is greater than the activity inhibiting PGF synthase. In particular, the ratio of the inhibitory activity for PGF synthase to the inhibitory activity for 15-PGDH for a given concentration, which activities are determined in particular by the concentrations which inhibit 50% of the enzymatic activity of PGF synthase $IC_{50}sf$ and of 15-PGDH $IC_{50}dh$ respectively, is at least greater than 1 and in particular at least 3:1, advantageously greater than or equal to 5:1. The preferred compounds of the invention exhibit an $IC_{50}sf/IC_{50}dh$ ratio of greater than or equal to 10:1.

"At least one" according to the invention means one or more (2, 3 or more). In particular, the composition can comprise one or more compounds of formula (I). This or these compounds can be cis or trans or Z or E isomers or a mixture of cis/trans or Z/E isomers. They can also be in the tautomeric form. In particular, the heterocycle Hy can be in the cis or trans or Z or E position and better still in the Z position of the adjacent double bond. This or these compounds can be enantiomers and/or diastereoisomers or a mixture of these isomers, in particular a racemic mixture.

The term "alkyl radical" is understood to mean, within the meaning of the invention, a hydrocarbonaceous radical which can be saturated or unsaturated and linear or branched. The alkyl radical preferably comprises from 1 to 10 carbon atoms. Mention may be made, as example of an alkyl radical which can be used in the invention, of the methyl, ethyl, isopropyl, n-butyl, tert-butyl, n-hexyl, 2-ethylhexyl, ethylene or propylene radicals. This radical can optionally be substituted, in particular by $OR_0$, with $R_0$ being H or a saturated, linear or branched, $C_1$-$C_{20}$, better still $C_1$-$C_{10}$, for example $C_1$-$C_5$, alkyl radical.

According to the invention, the heteroatom or heteroatoms of Hy can be O, N, S, P, Si or Se and in particular O, N or S. The heterocycle Hy can be saturated or unsaturated. In addition, it can comprise 4, 5, 6 or 7 atoms and one or more carbonyl or thiocarbonyl functional groups or both, the carbon of these functional groups forming part of the heterocycle.

In a specific embodiment of the invention, Hy represents an aromatic ring with 5 atoms comprising, as heteroatom, sulphur, nitrogen and their combinations. In addition, this heterocycle Hy comprises one or two carbonyl groups, the carbon of which groups forms part of the heterocycle. By way of example, this heterocycle exhibits the following formula (II):

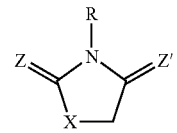

where Z, Z' and X independently represent S or O and R represents H or a saturated, linear or branched, $C_1$-$C_{10}$ alkyl radical. X can also represent NH. Advantageously, Z and Z' represent oxygen, which corresponds to a 1,3-thiazolidine-2,4-dione ring.

According to the invention, the rings employed as substituent ($S_1$) comprise from 4 to 7 atoms and better still from 5 to 6 atoms. They can be saturated or unsaturated and can optionally comprise one or more heteroatoms, such as S, N, O or their combinations. Furthermore, these rings can be alone or fused to another ring with the same or different chemical structure. When they are fused, they form condensed rings.

Mention may be made, as saturated hydrocarbonaceous rings which can be used, of the cyclopentyl or cyclohexyl radical and mention may be made, as unsaturated hydrocarbonaceous rings, of the cyclohexenyl or phenyl ring. Mention may be made, as fused hydrocarbonaceous rings, of the naphthyl radical. Mention may be made, as heterocycle, of the pyridine, piperidine, morpholine, pyrrole, furan or thiazole rings. In addition, these rings can be substituted by one or more substituents having the definition indicated above for R or $R_0$.

According to the invention, the compounds of formula (I) are in the isolated form, that is to say nonpolymeric form. They are phenylfurans, phenylthiophenes or phenylpyrroles. In addition, $R_1$ can be situated in the 3- or 4-position, G being regarded as the 1-position of the heterocycle with 5 atoms. Furthermore, $R_2$ and $R_3$ can be situated in any position of the phenyl ring carrying them and in particular in the para- or meta-position with regard to the following part (A):

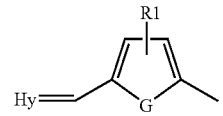

Preferably, $R_1$ represents a hydrogen atom.

Advantageously, at least one of the $R_2$ and $R_3$ groups represent $CF_3$, $OR_0$ or $COOR_0$ with $R_0$ being H or a saturated or unsaturated, linear or branched, $C_1$-$C_{20}$, better still $C_1$-$C_{10}$, alkyl radical. Mention may be made, as example of alkyl radical which can be used, of methyl, ethyl, tert-butyl, isopropyl, n-butyl or n-hexyl. In particular, $COOR_0$ represents COOH or $COOCH_2$—$CH_3$. In addition, $OR_0$ represents in particular OH or $OCH_3$. In particular, $R_2$ represents COOH or OH and $R_3$ represents H; $R_2$ represents $COOCH_2$—$CH_3$ and $R_3$ represents H; or $R_2$ and $R_3$ represent $CF_3$ or $OCH_3$.

The term "salts of compound of formula (I)" is understood to mean, according to the invention, the organic or inorganic and single or double salts of a compound of formula (I).

Mention may be made, as inorganic salts which can be used according to the invention, of: single or double sodium or potassium salts and salts of zinc ($Zn^{2+}$), of calcium ($Ca^{2+}$), of copper ($Cu^{2+}$), of iron ($Fe^{2+}$), of strontium ($Sr^{2+}$), of magnesium ($Mg^{2+}$), of ammonium and of manganese ($Mn^{2+}$); hydroxides, carbonates, halides (such as chlorides), sulphates, nitrates or phosphates. Preferably, the salt is a sodium salt.

The organic salts which can be used according to the invention are, for example, triethanolamine, monoethanolamine, diethanolamine, hexadecylamine, N,N,N',N'-tetrakis (2-hydroxypropyl)ethylenediamine or tris(hydroxymethyl) aminomethane salts.

According to a specific embodiment of the invention, the heterocyclic compounds to which the invention applies exhibit the following formula (III) and better still the following formula (IIIa) or the corresponding salt (mono- or disalt) form:

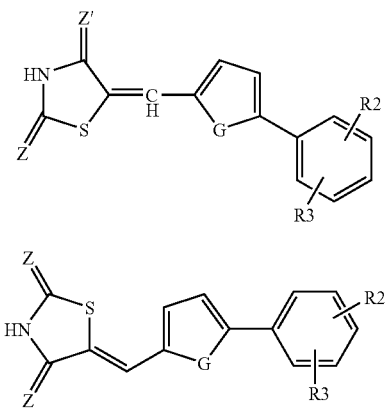

(III)

(IIIa)

in which Z, Z' and G independently represent O or S; and at least one of the $R_2$ and $R_3$ groups represent $CF_3$, $OR_0$ or $COOR_0$ with $R_0$ being H or a saturated or unsaturated, linear or branched, $C_1$-$C_{20}$, better still $C_1$-$C_{10}$, alkyl radical.

Another subject-matter of the invention is a novel heterocyclic compound of following formula (IV) or in the form of one of its salts, exhibiting in particular the property of inhibiting 15-PGDH and/or of preserving the amount and/or the activity of prostaglandins, in particular in the human hair follicle:

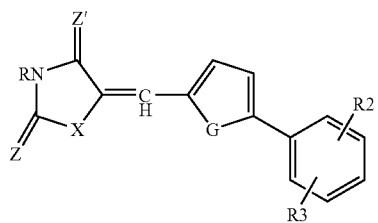

in which Z, Z' and G independently represent O or S; X represents O, NH or S; R represents hydrogen or a saturated, linear or branched, $C_1$-$C_{10}$ alkyl radical; and at least one of the $R_2$ and $R_3$ groups represent a hydrogen, CN, $NO_2$, $CF_3$, a phenyl, $OR_0$ or $COOR_0$ radical or a saturated, linear or branched, $C_1$-$C_{20}$, better still $C_1$-$C_{10}$, alkyl radical option- ally substituted by $OR_0$ with $R_0$ being H or a saturated, linear or branched, $C_1$-$C_{20}$, better still $C_1$-$C_{10}$, alkyl radical, provided that, when X=S and Z=Z'=G or Z≠Z', then $R_2$ and $R_3$ are other than COOH.

According to a specific embodiment, the heterocyclic compound exhibits the following formula (V) or a corresponding salt:

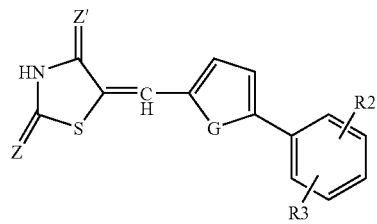

in which Z, Z' and G independently represent O or S; and at least one of the $R_2$ and $R_3$ groups represent phenyl, $NO_2$, $CF_3$, $OR_0$, $OR_0$, $COOR_0$ or a saturated, linear or branched, $C_1$-$C_{20}$, better still $C_1$-$C_{10}$, alkyl radical optionally substituted by $OR_0$ with $R_0$ being H or a saturated, linear or branched, $C_1$-$C_{20}$, better still $C_1$-$C_{10}$, alkyl radical, provided that, when Z=Z'=G or Z≠Z', then $R_2$ and $R_3$ are other than COOH.

Advantageously, when Z=Z'=G, at least one of the $R_2$ and $R_3$ groups represents $CF_3$, $OR_0$ or $COOR_0$ with $R_0$ being a saturated, linear or branched, $C_1$-$C_{10}$, better still $C_1$-$C_5$, alkyl radical. According to another preferred embodiment of the invention, when Z=Z' and are different from G, at least one of the $R_2$ and $R_3$ groups represents $CF_3$ or $COOR_0$ with $R_0$ being H.

According to another embodiment of the invention, the heterocyclic compound exhibits the following formula (VI) or a corresponding salt form:

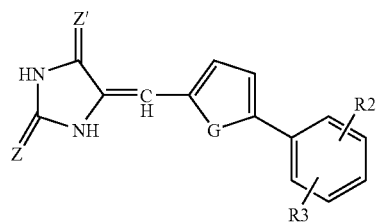

in which Z, Z' and G independently represent O or S; and at least one of the $R_2$ and $R_3$ groups represent a hydrogen, CN, $CF_3$, $NO_2$, $OR_0$, $COOR_0$ or a saturated, linear or branched, $C_1$-$C_{20}$, better still $C_1$-$C_{10}$, alkyl radical optionally substituted by $OR_0$ with $R_0$ being H or a saturated, linear or branched, $C_1$-$C_{20}$, better still $C_1$-$C_{10}$, alkyl radical.

According to another embodiment of the invention, the heterocyclic compound exhibits the following formula (VII) or the corresponding salt form:

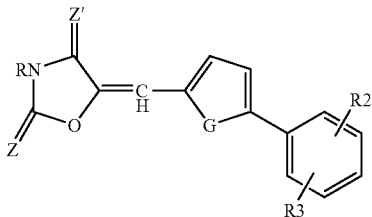

in which Z, Z' and G independently represent O or S; R represents a saturated, linear or branched, $C_1$-$C_{10}$ alkyl radical; and at least one of the $R_2$ and $R_3$ groups represent a saturated, linear or branched, $C_1$-$C_{20}$, better still $C_1$-$C_{10}$, alkyl radical, $NO_2$ or $OR_0$ with $R_0$ being H or a saturated, linear or branched, $C_1$-$C_{20}$, better still $C_1$-$C_{10}$, alkyl radical.

Preferably, the heterocyclic compound of the invention is in the Z form.

To the knowledge of the Applicant, no document of the prior art discloses or suggests that the heterocyclic compounds of formula (I) or one of their salts have the property of inducing and/or stimulating the growth of human keratinous fibres and in particular of the hair and eyelashes and/or slowing down their loss, or that these compounds can be used topically to increase the density of human keratinous fibres and more especially that of the hair and eyelashes.

The compounds of formula (I) or their salts can be manufactured in a known way as disclosed in the document WO 01/066541. The compounds of formula (I) are solid at ambient temperature.

The effective amount of a compound of formula (I) or of one of its salts corresponds to the amount necessary to obtain the desired result (namely, to increase the density of keratinous fibres and in particular of the hair and eyelashes or to promote their growth). A person skilled in the art is therefore in a position to evaluate this effective amount, which depends on the nature of the compound used, on the person to which it is applied and on the time of this application.

In the continuation of the text, unless otherwise indicated, the amounts of the various ingredients of the composition are given as percentage by weight with respect to the total weight of the composition.

To give an order of magnitude, according to the invention, the compound of formula (I) or one of its salts or a mixture of compounds of formula (I) and/or of their salts can be used in an amount representing from $10^{-3}$% to 10% of the total weight of the composition and preferably in an amount representing from $10^{-3}$% to 5% and better still from $10^{-2}$% to 2% of the total weight of the composition, for example from 0.5 to 2%.

The composition of the invention can be for cosmetic or pharmaceutical use. Preferably, the composition of the invention is for cosmetic use. Consequently, the composition should comprise a physiologically acceptable medium which is non-toxic and which is capable of being applied to human skin, including the scalp and eyelids, and to human keratinous fibres. The term "cosmetic" is understood to mean, within the meaning of the invention, a composition with a pleasant appearance, smell and feel.

The compound of formula (I), which may or may not be salified, can be used in a composition which has to be ingested, injected or applied to the skin or to keratinous fibres (over any cutaneous region or all of the fibres to be treated).

According to the invention, the compound of formula (I) or one of its salts can be used orally in an amount of 0.1 to 300 mg per day, for example of 5 to 10 mg/day.

A preferred composition of the invention is a composition for cosmetic use and in particular for topical application to the skin and keratinous fibres and more especially to the scalp, hair and eyelashes.

Consequently, another subject-matter of the invention is a composition for caring for or making up keratinous fibres, in particular a haircare or mascara composition, for topical application comprising a physiologically acceptable medium and an effective amount of at least one compound of formula (I) or of one of these salts, as described above.

This composition can be provided in any known dosage form which is suited to the method of use.

For topical application to the skin, the composition can have the form of an aqueous, alcoholic or aqueous/alcoholic solution or suspension or of an oily suspension, of an emulsion with a more or less fluid consistency and in particular a liquid or semi-liquid consistency, obtained by dispersion of a fatty phase in an aqueous phase (O/W) or vice versa (W/O), of an (O/W) or (W/O) solid emulsion, of an aqueous, aqueous/alcoholic or oily gel which is more or less fluid or solid, of a free or compact powder to be used as is or to be incorporated in a physiologically acceptable medium, or also of microcapsules or micro-particles, or of vesicular dispersions of ionic and/or nonionic type.

It is also possible to envisage a composition in the form of a foam or in the form of a spray or aerosol then comprising a pressurized propellant.

It can thus be provided in the form of a lotion, serum, milk, O/W or W/O cream, gel, ointment, pomade, powder, balm, patch, impregnated pad, cake or foam.

In particular, the composition for application to the scalp or hair can be provided in the form of a hair care lotion, for example for daily or twice-weekly application, of a shampoo or of a hair conditioner, in particular for twice-weekly or weekly application, of a liquid or solid soap for cleaning the scalp, for daily application, of a product for shaping the hairstyle (lacquer, hairsetting product, styling gel), of a treatment mask, of a cream or of a foaming gel for cleaning the hair. It can also be provided in the form of a hair dye or mascara to be applied with a brush or comb.

Furthermore, for application to the eyelashes or body hairs, the composition to which the invention applies can be provided in the form of a pigmented or nonpigmented mascara, to be applied with a brush to the eyelashes or alternatively to the beard or moustache hairs.

For a composition for use by injection, the composition can be provided in the form of an aqueous lotion or of an oily suspension. For use by the oral route, the composition can be provided in the form of capsules, of granules, of syrups to be taken orally or of tablets.

According to a specific embodiment, the composition according to the invention is provided in the form of a hair cream or lotion, of a shampoo, of a hair conditioner, of a hair mascara or of a mascara for the eyelashes.

The amounts of the various constituents of the composition according to the invention are those generally used in the fields under consideration. In addition, these compositions are prepared according to conventional methods.

When the composition is an emulsion, the proportion of the fatty phase can range from 2% to 80% by weight and preferably from 5% to 50% by weight with respect to the total weight of the composition. The aqueous phase is adjusted according to the content of fatty phase and of compound(s) (I) and according to the content of possible additional ingredients, in order to obtain 100% by weight. In practice, the aqueous phase represents from 5 to 99.9%.

The fatty phase can comprise fatty or oily compounds which are liquid at ambient temperature (25° C.) and atmospheric pressure (760 mmHg), generally known as oils. These oils may or may not be compatible with one another and may form a macroscopically homogeneous liquid fatty phase or a two- or three-phase system.

The fatty phase can, in addition to the oils, comprise waxes, gums, lipophilic polymers, or "pasty" or viscous products comprising solid parts and liquid parts.

The aqueous phase comprises water and optionally an ingredient miscible in any proportion with water, such as lower $C_1$ to $C_8$ alcohols, for example ethanol or isopropanol, polyols, such as propylene glycol, glycerol or sorbitol, or else acetone or ether.

The emulsifiers and coemulsifiers used to produce a composition in the form of an emulsion are those generally used in the cosmetic and pharmaceutical fields. In addition, their nature depends on the sense of the emulsion. In practice, the emulsifier and optionally the coemulsifier are present in the composition in a proportion ranging from 0.1% to 30% by weight, preferably from 0.5 to 20% by weight and better still from 1 to 8%. In addition, the emulsion can comprise lipid vesicles and in particular liposomes.

When the composition is in the form of an oily solution or gel, the fatty phase can represent more than 90% of the total weight of the composition.

Advantageously, for a hair application, the composition is an aqueous, alcoholic or aqueous/alcoholic solution or suspension and better still a water/ethanol solution or suspension. The alcohol fraction can represent from 5 to 99.9% and better still from 8 to 80%.

For a mascara application, the composition of the invention is a wax-in-water or wax-in-oil dispersion, a gelled oil or an aqueous gel, with or without pigment.

The composition of the invention can comprise, in addition, other ingredients generally used in the fields concerned chosen from solvents, thickeners or gelling agents for the aqueous phase or for the oily phase, colouring materials which are soluble in the medium of the composition, solid particles of the filler or pigment type, antioxidants, preservatives, fragrances, electrolytes, neutralizing agents, film-forming polymers, UV blocking agents, such as sunscreens, cosmetic and pharmaceutical active principles with a beneficial effect on the skin or keratinous fibres, other than the compounds of formula (I), or their mixtures. These additives can be present in the composition according to the amounts generally used in the cosmetic and dermatological field and in particular in a proportion of 0.01 to 50% of the total weight of the composition and better still of 0.1 to 20% and, for example, of 0.1 to 10%. These additives, depending on their nature, can be introduced into the fatty phase, into the aqueous phase and/or into the lipid vesicles and in particular liposomes.

Of course, a person skilled in the art will take care to choose the possible additional additives and/or their amounts so that the advantageous properties of the composition according to the invention, namely the inhibition, in particular specific inhibition, of 15-PGDH and in particular the increase in the density of keratinous fibres (hair or eyelashes), are not, or not substantially, detrimentally affected by the envisaged addition.

Mention may be made, as solvents which can be used in the invention, of lower $C_2$ to $C_8$ alcohols, such as ethanol or isopropanol, propylene glycol and certain light cosmetic oils, such as $C_6$ to $C_{16}$ alkanes.

Mention may be made, as oils which can be used in the invention, of oils of mineral origin (liquid petrolatum, hydrogenated isoparaffin), oils of vegetable origin (liquid fraction of karite butter, sunflower oil, apricot oil, fatty alcohol or fatty acid), oils of animal origin (perhydrosqualene), synthetic oils (fatty acid esters, purcellin oil), silicone oils (phenyltrimethicone, linear or cyclic polydimethylsiloxane) and fluorinated oils (perfluoropolyethers). Mention may be made, as waxes, of silicone waxes, beeswax, rice wax, candelilla wax, carnauba wax, paraffin wax or polyethylene wax.

Mention may be made, as emulsifiers which can be used in the invention, of, for example, glyceryl stearate or laurate, sorbitol stearates or oleates, alkyl dimethicone copolyols (with alkyl $\geq 8$) and their mixtures for a W/O emulsion. Use may also be made of polyethylene glycol monostearate or monolaurate, polyoxyethylenated sorbitol stearate or oleate, dimethicone copolyols and their mixtures for an O/W emulsion.

Mention may be made, as hydrophilic gelling agents which can be used in the invention, of carboxyvinyl polymers (carbomer), acrylic copolymers, such as acrylate/alkyl acrylate copolymers, polyacrylamides, polysaccharides, such as hydroxypropylcellulose, natural gums and clays and mention may be made, as lipophilic gelling agents, of modified clays, such as bentones, metal salts of fatty acids, such as aluminium stearates, hydrophobic treated silica, ethylcellulose or their mixtures.

The composition can additionally comprise a cosmetic or pharmaceutical active principle other than the compounds of formula (I) which can be hydrophilic and is chosen from proteins, protein hydrolysates, amino acids, polyols, urea, allantoin, sugars and sugar derivatives, water-soluble vitamins, plant extracts (those of Iridaceae or of soya) and hydroxy acids, such as fruit acids or salicylic acid; or lipophilic and is chosen from retinol (vitamin A) and its derivatives, in particular ester (retinol palmitate), tocopherol (vitamin E) and its derivatives, in particular ester (tocopherol acetate), essential fatty acids, ceramides, essential oils, salicylic acid derivatives, such as 5-(n-octanoyl)salicylic acid, esters of hydroxy acids, phospholipids, such as lecithin, or their mixtures.

According to a specific embodiment of the invention, the compound of formula (I) or one of its salts can be combined with at least one additional active compound which promotes the regrowth and/or which limits the loss of keratinous fibres (hair, eyelashes). These additional compounds are chosen in particular from lipoxygenase inhibitors, such as disclosed in EP 0 648 488, bradykinin inhibitors, disclosed in particular in EP 0 845 700, prostaglandins and their derivatives, in particular those disclosed in WO 98/33497, WO 95/11003, JP 9.7-100091 or JP 96-134242, prostaglandin receptor agonists or antagonists, nonprostanoic prostaglandin analogues, such as disclosed in EP 1 175 891 and EP 1 175 890, WO 01/74307, WO 01/74313, WO 01/74314, WO 01/74315 or WO 01/72268, or their mixtures.

Mention may be made, as other additional active agents which promote the growth of keratinous fibres (in particular of the hair) and/or which limit their loss which can be present in the composition according to the invention, of vasodilators, antiandrogens, cyclosporins and their analogues, antimicrobials and antifungals, anti-inflammatories or retinoids, alone or as a mixture.

The vasodilators which can be used are in particular potassium channel agonists, including minoxidil and the compounds disclosed in U.S. Pat. Nos. 3,382,247, 5,756,092, 5,772,990, 5,760,043, 5,466,694, 5,438,058 or 4,973,474, cromakalim, nicorandil and diaxozide, alone or in combination.

The antiandrogens which can be used include in particular steroidal or nonsteroidal inhibitors of 5α-reductase, such as finasteride and the compounds disclosed in U.S. Pat. No. 5,516,779, cyprosterone acetate, azelaic acid, its salts and its derivatives and the compounds disclosed in U.S. Pat. No. 5,480,913, flutamide, oxendolone, spironolactone, diethylstilbestrol and the compounds disclosed in U.S. Pat. Nos. 5,411,981, 5,565,467 and 4,910,226.

The antimicrobial or antifungal compounds can be chosen from selenium derivatives, octopirox, ketoconazole, triclocarban, triclosan, zinc pyrithione, itraconazole, asiatic acid, hinokitiol, mipirocin, tetracyclines, in particular erythromycin and the compounds disclosed in EP 0 680 745, clinycin hydrochloride, benzoyl peroxide or benzyl peroxide, minocyclin and the compounds belonging to the class of the imidazoles, such as econazole, ketoconazole or miconazole or their salts, or nicotinic acid esters, including in particular tocopherol nicotinate, benzyl nicotinate and $C_1$-$C_6$ alkyl nicotinates, such as methyl nicotinate or hexyl nicotinate.

The anti-inflammatories can be chosen from steroidal anti-inflammatories, such as glucocorticoids or corticosteroids (for example: hydrocortisone), and nonsteroidal anti-inflammatories, such as glycyrrhetinic acid and α-bisabolol, benzydamine, salicylic acid and the compounds disclosed in EP 0 770 399, WO 94/06434 and FR 2 268 523.

The retinoids can be chosen from isotretinoin, acitretin and tazarotene.

Mention may be made, as other active compounds for promoting the growth and/or limiting the loss of the hair which can be used in combinations with the compound of formula (I), of aminexil, 6-O-[(9Z,12Z)-octadeca-9,12-dienoyl]hexapyranose, benzalkonium chloride, benzethonium chloride, phenol, oestradiol, chlorpheniramine maleate, chlorophyllin derivatives, cholesterol, cysteine, methionine, menthol, peppermint oil, calcium panthotenate, panthenol, resorcinol, protein kinase C activators, glycosidase inhibitors, glycosaminoglycanase inhibitors, pyroglutamic acid esters, hexosaccharidic acid or acylhexosaccharic acid, arylsubstituted ethylenes, N-acylated amino acids, flavonoids, ascomycin derivatives and analogues, histamine antagonists, saponins, proteoglycanase inhibitors, oestrogen agonists and antagonists, pseudopterins, cytokines and growth factor promoters, IL-1 or IL-6 inhibitors, IL-10 promoters, TNF inhibitors, benzozphenones and hydantoin, retinoic acid; vitamins, such as vitamin D, analogues of vitamin B12 and panthotenol; triterpenes, such as ursolic acid and the compounds disclosed in U.S. Pat. No. 5,529,769, U.S. Pat. No. 5,468,888 or U.S. Pat. No. 5,631,282; antipruritic agents, such as thenaldine, trimeprazine or cyproheptadine; agents for combating parasites, in particular metronidazole, crotamiton or pyrethroids; calcium antagonist agents, such as cinnarizine, diltiazem, nimodipine, verapamil and nifedipine; hormones, such as oestriol or its analogues, thyroxine and its salts, or progesterone; FP receptor (receptor to prostaglandins of the F type) agonists, such as latanoprost, bimatroprost, travoprost or unoprostone; and their mixtures.

Advantageously, the composition according to the invention will comprise at least one 15-PGDH inhibitor as defined above and at least one prostaglandin or one prostaglandin derivative, such as, for example, prostaglandins of the 2 series, including in particular $PGF_{2\alpha}$ and $PGE_2$, in the salt or ester form (example, the isopropyl esters), their derivatives, such as 16,16-dimethyl-$PGE_2$, 17-phenyl-$PGE_2$, 16,16-dimethyl-$PGF_{2\alpha}$ or 17-phenyl-$PGF_{2\alpha}$, or prostaglandins of the 1 series, such as 11-deoxy-prostaglandin $E_1$ or 1-deoxyprostaglandin $E_1$, in the salt or ester form, their analogues, in particular latanoprost, travoprost, bimatoprost, fluprostenol, cloprostenol, viprostol, butaprost, misoprostol or unoprostone, their salts or their esters.

Preferably, the composition comprises at least one non-prostanoic agonist of the EP2 and/or EP4 receptors, in particular as disclosed in EP 1 175 892.

It is also possible to envisage that the composition comprising at least the compound of formula (I), which may or may not be salified, is in the liposomed form, such as disclosed in particular in the document WO 94/22468. Thus, the compound encapsulated in the liposomes can be delivered selectively to the hair follicle or the base of the eyelash.

The composition according to the invention can be applied to the areas of the scalp and hair of an individual which are suffering from alopecia and can optionally be left in contact for several hours and can optionally be rinsed.

It is possible, for example, to apply the composition comprising an effective amount of a compound of formula (I), which may or may not be salified, in the evening, to keep this composition in contact overnight and optionally to clean the fibres, such as to shampoo, on the following morning. These applications can be repeated daily for one or more months, depending on the individual.

Advantageously, in the process according to the invention, between 5 and 500 µl of a solution or composition as defined above, comprising between 0.001% and 5% of 15-PGDH inhibitor, are applied to the areas of the scalp to be treated.

Implementational examples of the invention will now be given by way of illustration, which examples should in no way limit the scope of the invention.

EXAMPLES

Mention may be made, as examples of heterocyclic compounds of formula (I) which can be used in the invention, of the following compounds:

Compound 1: 4-{5-[(2,4-Dioxo-1,3-thiazolidin-5-ylidene)methyl]-2-furyl}benzoic acid

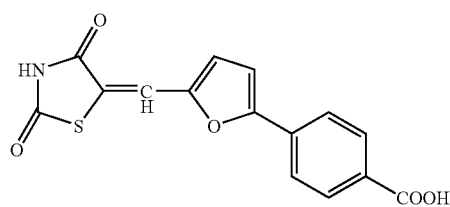

and more specifically the compound 1a:

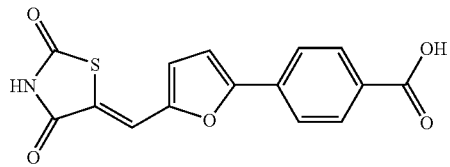

Compound 2: Ethyl 4-{5-[(2,4-dioxo-1,3-thiazolidin-5-ylidene)methyl]-2-furyl}benzoate

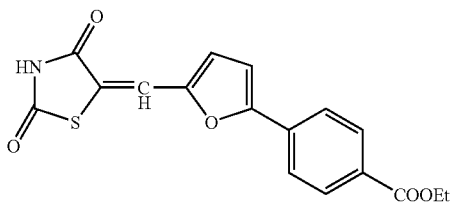

Compound 3: 5-({5-[3,5-bis(Trifluoromethyl)phenyl]-2-furyl}methylene)-1,3-thiazolidine-2,4-dione

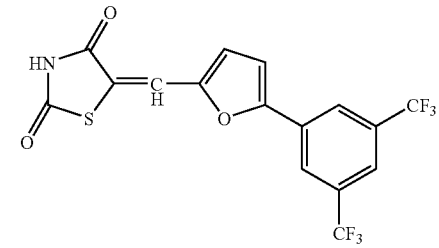

Compound 4: 3-{5-[(2,4-Dioxo-1,3-thiazolidin-5-ylidene)methyl]-2-furyl}benzoic acid

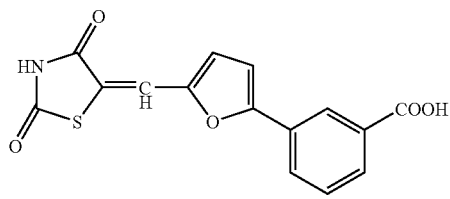

Compound 5: 4-{5-[(2,4-Dioxo-1,3-thiazolidin-5-ylidene)methyl]-2-thiophenyl}benzoic acid

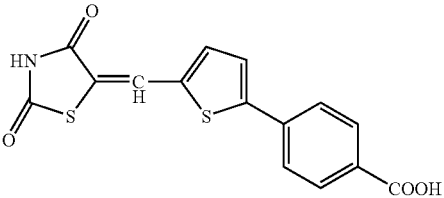

Compound 6: 4-{5-[(2-Sulpho-4-oxo-1,3-thiazolidin-5-ylidene)methyl]-2-furyl}benzoic acid

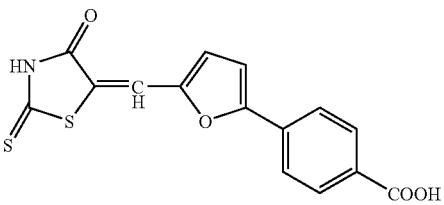

Compound 7: 4-{5-[(2,4-Disulpho-1,3-thiazolidin-5-ylidene)methyl]-2-furyl}benzoic acid

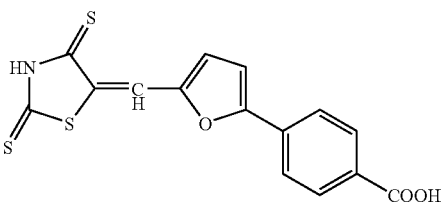

Compound 8: Disodium salt of 4-{5-[(2,4-disulpho-1,3-thiazolidin-5-ylidene)methyl]-2-furyl}benzoic acid (isomer Z)

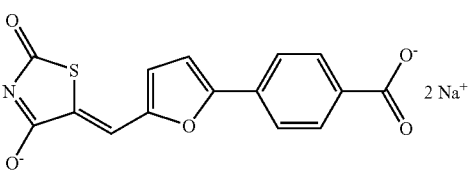

The compound of formula (I) is advantageously the disodium salt of 4-{5-[(2,4-disulpho-1,3-thiazolidin-5-ylidene)methyl]-2-furyl}benzoic acid and in particular the isomer in the Z form.

Mention may also be made, as other compounds of formula (I) which can be used in the invention, of:

| Heterocyclic structure D | Appearance | LC purity* | MS** | Name |
|---|---|---|---|---|
| 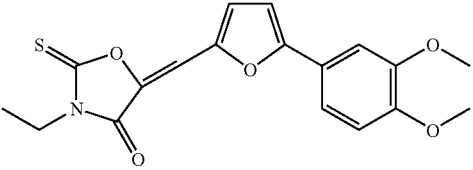<br>Compound D1 | russet powder | 93 | M + H<br>M + Na | 5-[5-(3,4-Dimethoxyphenyl)furan-2-yl-methylene]-3-ethyl-2-thioxo-oxazolidin-4-one |
| 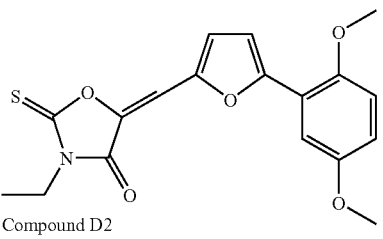<br>Compound D2 | red powder | 100 | M + Na | 5-[5-(2,5-Dimethoxyphenyl)furan-2-yl-methylene]-3-ethyl-2-thioxo-oxazolidin-4-one |
| 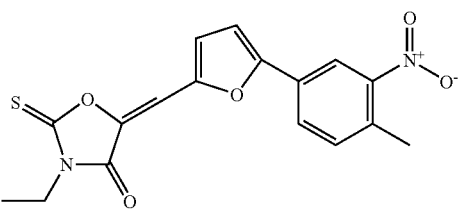<br>Compound D3 | red powder | 100 | M − H<br>M + Na | 3-Ethyl-5-[5-(4-methyl-3-nitro-phenyl)furan-2-yl-methylene]-2-thioxo-oxazolidin-4-one |

| Heterocyclic structure E | Appearance | LC purity | MS | Name |
|---|---|---|---|---|
| 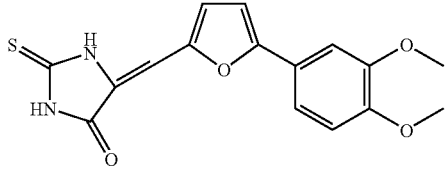<br>Compound E1 | red powder | 91 | M + H<br>M + Na<br>M − H | 5-[5-(3,4-Dimethoxy-phenyl)furan-2-yl-methylene]-2-thioxoimidazolidin-4-one |
| 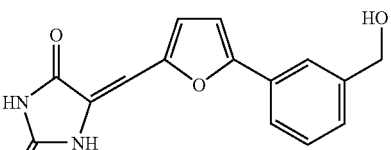<br>Compound E2 | red gum | 100 | M + H<br>M − H | 5-[5-(3-(Hydroxymethyl)-phenyl)furan-2-yl-methylene]-2-thioxo-imidazolidin-4-one |
| 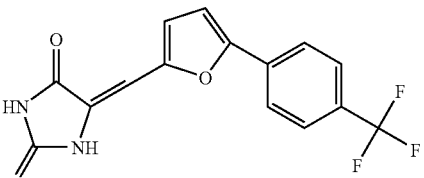<br>Compound E3 | orange solid | 100 | M − H | 2-Thioxo-5-[5-(4-(trifluoromethyl)-phenyl)-furan-2-yl-methylene]-imidazolidin-4-one |

-continued

| | | | | |
|---|---|---|---|---|
| 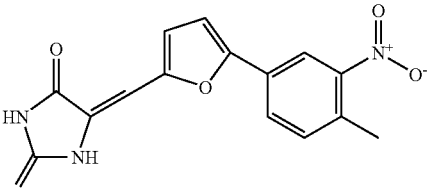
Compound E4 | red powder | 73 | M − H | 5-[5-(4-Methyl-3-nitrophenyl)-furan-2-yl-methylene]-2-thioxo-imidazolidin-4-one |
| 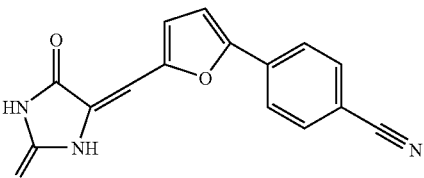
Compound E5 | brown powder | 93 | M − H | 4-[5-Oxo-2-thioxo-imidazolidin-4-ylidene-methyl)furan-2-yl]benzo-nitrile |
| 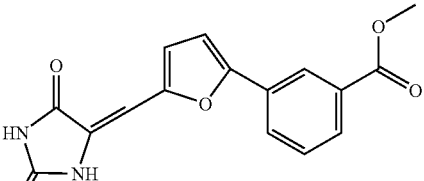
Compound E6 | orange powder | 89 | M + H<br>M + Na<br>M − H | 3-[5-(5-Oxo-2-thioxo-imidazolidin-4-ylidene-methyl)furan-2-yl]benzoic acid methyl ester |
| 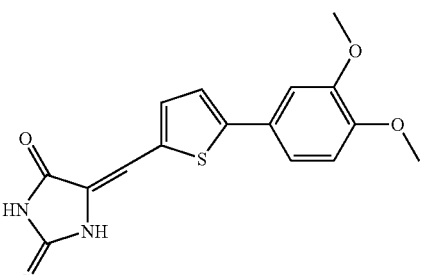
Compound E7 | brown powder | 100 | M − H | 5-[5-(3,4-Dimethoxy-phenyl)thio-phen-2-yl-methylene)-2-thioxo-imidazolidin-4-one |
| 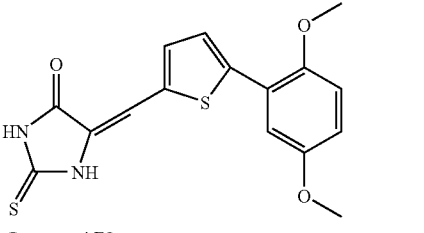
Compound E8 | maroon powder | 65 | M − H | 5-[5-(2,5-Dimethoxy-phenyl)-thiophen-2-ylmethylene]-2-thioxo-imidazolidin-4-one |
| 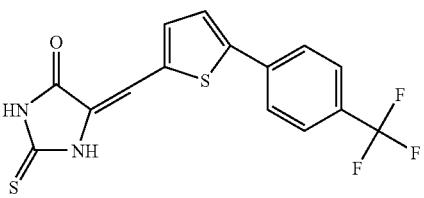
Compound E9 | orange powder | 90 | M − H | 2-Thioxo-5-[5-(4-(tri-fluoromethyl)-phenyl)thio-phen-2-yl-methylene]-imidazolidin-4-one |

-continued

| | | | | |
|---|---|---|---|---|
| 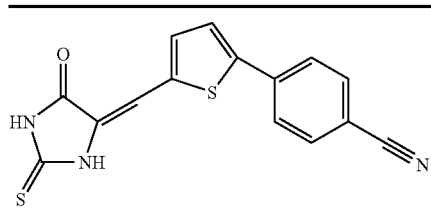<br>Compound E10 | black powder | 66 | M − H | 4-[5-(5-Oxo-2-thioxo-imidazolidin-4-ylidene-methyl)-thiophen-2-yl]benzonitrile |
| 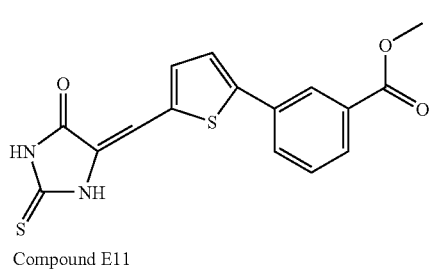<br>Compound E11 | brown powder | 90 | M − H | 3-[5-(5-Oxo-2-thioxo-imidazolidin-4-ylidene-methyl)-thiophen-2-yl]benzoic acid methyl ester |
| 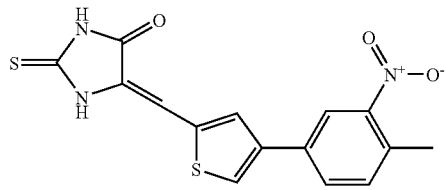<br>Compound E12 | orange powder | 64 | M − H | 5-[4-(4-Methyl-3-nitrophenyl)-thiophen-2-ylmethylene]-2-thioxo-imidazolidin-4-one |
| 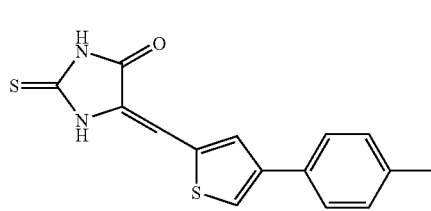<br>Compound E13 | yellow powder | 53 | M − H | 4-[5-(5-Oxo-2-thioxo-imidazolidin-4-ylidene-methyl)-thiophen-3-yl]benzonitrile |
| 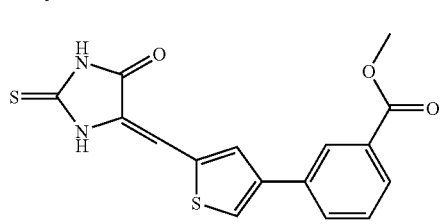<br>Compound E14 | yellow powder | 91 | M − H | 3-[5-(5-Oxo-2-thioxo-imidazolidin-4-ylidene-methyl)-thiophen-3-yl]benzoic acid methyl ester |
| 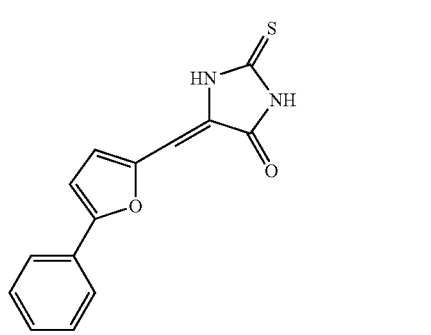<br>Compound E15 | red gum | 90 | M − H | 5-(5-Phenyl-furan-2-yl-methylene)-2-thioxo-imidazolidin-4-one |

-continued

| | Appearance | LC purity | MS | Name |
|---|---|---|---|---|
| 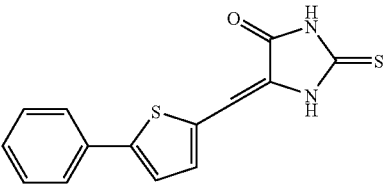<br>Compound E16 | orange solid | 81 | M − H | 5-(5-Phenyl-thiophen-2-ylmethylene)-2-thioxo-imidazolidin-4-one |

| Heterocyclic structure F | Appearance | LC purity | MS | Name |
|---|---|---|---|---|
| 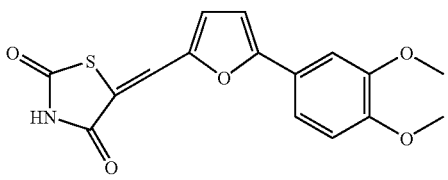<br>Compound F1 | orange powder | 90 | M − H | 5-[5-(3,4-Dimethoxy-phenyl)furan-2-ylmethylene]-thiazolidine-2,4-dione |
| 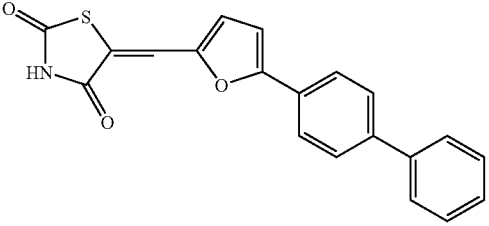<br>Compound F2 | yellow powder | 88 | M − H | 5-(5-(Biphenyl-4-yl)furan-2-ylmethylene)-thiazolidine-2,4-dione |
| 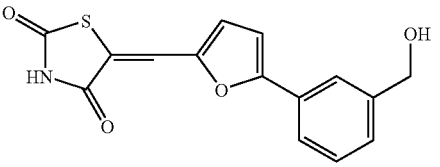<br>Compound F3 | yellow powder | 91 | M − H | 5-[5-(3-(Hydroxy-methyl)-phenyl)furan-2-yl-methylene]-thiazolidine-2,4-dione |
| 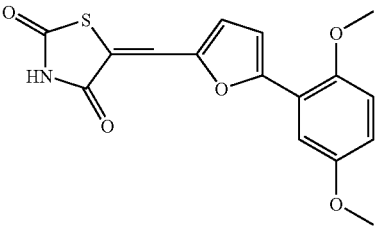<br>Compound F4 | orange cotton | 100.00 | M − H | 5-[5-(2,5-Dimethoxy-phenyl)furan-2-yl-methylene]-thiazolidine-2,4-dione |
| 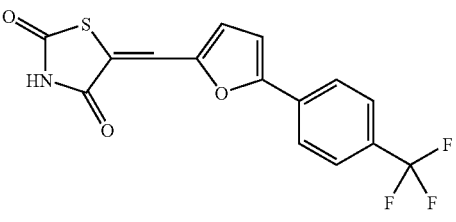<br>Compound F5 | yellow powder | 100 | M − H | 5-[5-(4-(Trifluoro-methyl)-phenyl)furan-2-yl-methylene]-thiazolidine-2,4-dione |

-continued

| | | | | |
|---|---|---|---|---|
| 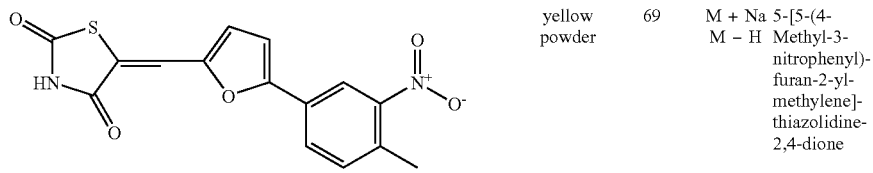<br>Compound F6 | yellow powder | 69 | M + Na<br>M − H | 5-[5-(4-Methyl-3-nitrophenyl)-furan-2-yl-methylene]-thiazolidine-2,4-dione |
| 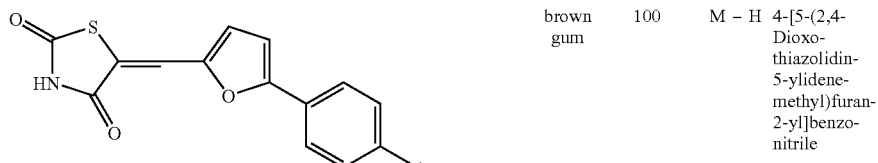<br>Compound F7 | brown gum | 100 | M − H | 4-[5-(2,4-Dioxo-thiazolidin-5-ylidene-methyl)furan-2-yl]benzo-nitrile |
| 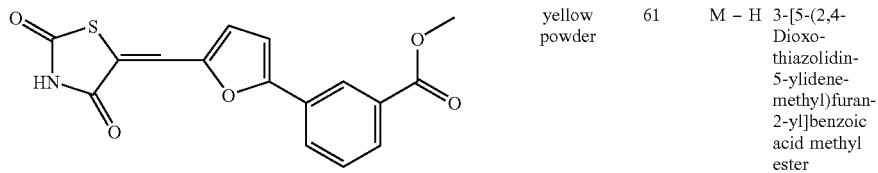<br>Compound F8 | yellow powder | 61 | M − H | 3-[5-(2,4-Dioxo-thiazolidin-5-ylidene-methyl)furan-2-yl]benzoic acid methyl ester |
| 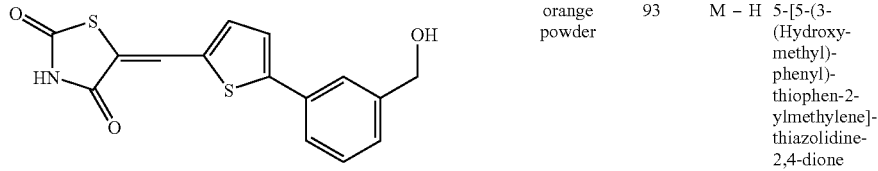<br>Compound F9 | orange powder | 93 | M − H | 5-[5-(3-(Hydroxy-methyl)-phenyl)-thiophen-2-ylmethylene]-thiazolidine-2,4-dione |
| 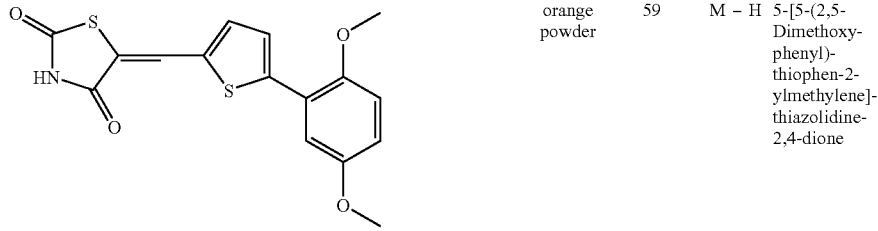<br>Compound F10 | orange powder | 59 | M − H | 5-[5-(2,5-Dimethoxy-phenyl)-thiophen-2-ylmethylene]-thiazolidine-2,4-dione |
| 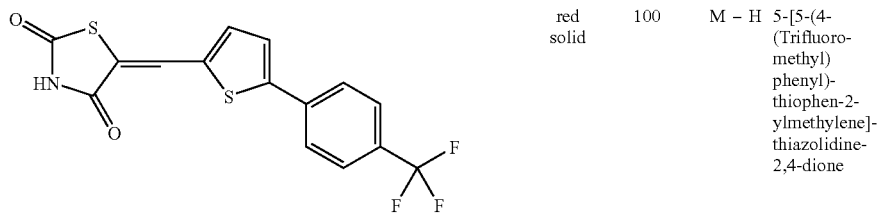<br>Compound F11 | red solid | 100 | M − H | 5-[5-(4-(Trifluoro-methyl)phenyl)-thiophen-2-ylmethylene]-thiazolidine-2,4-dione |

-continued

| | | | | |
|---|---|---|---|---|
| 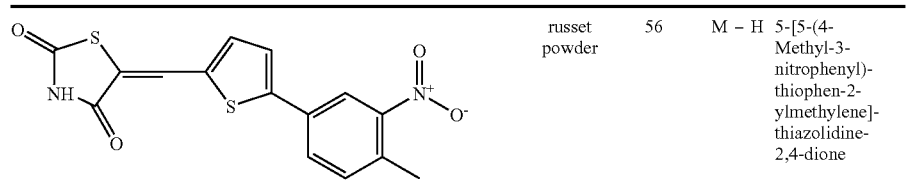  Compound F12 | russet powder | 56 | M − H | 5-[5-(4-Methyl-3-nitrophenyl)-thiophen-2-ylmethylene]-thiazolidine-2,4-dione |
| 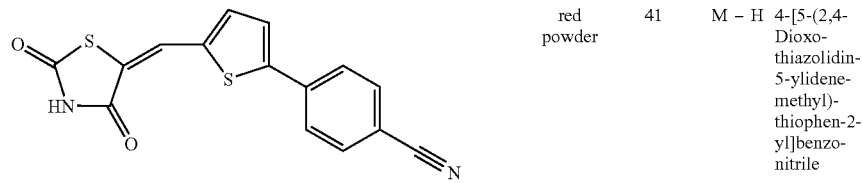  Compound F13 | red powder | 41 | M − H | 4-[5-(2,4-Dioxo-thiazolidin-5-ylidene-methyl)-thiophen-2-yl]benzo-nitrile |
| 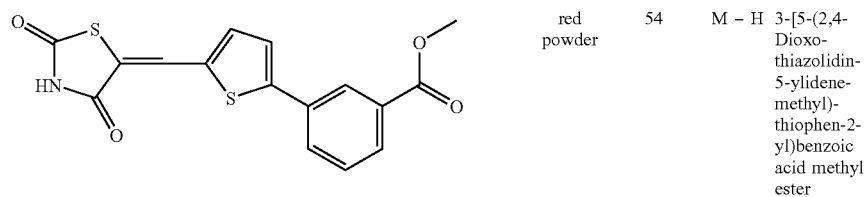  Compound F14 | red powder | 54 | M − H | 3-[5-(2,4-Dioxo-thiazolidin-5-ylidene-methyl)-thiophen-2-yl)benzoic acid methyl ester |
| 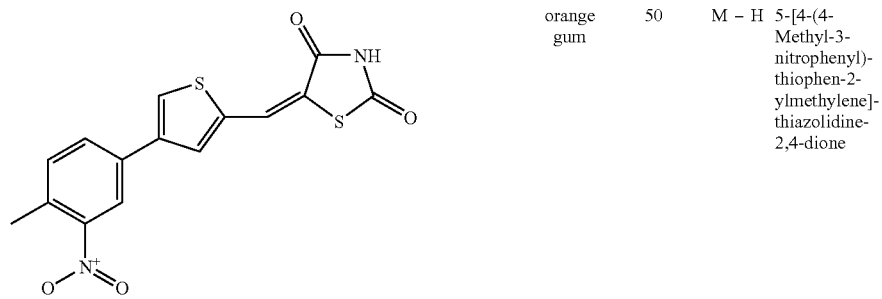  Compound F15 | orange gum | 50 | M − H | 5-[4-(4-Methyl-3-nitrophenyl)-thiophen-2-ylmethylene]-thiazolidine-2,4-dione |
| 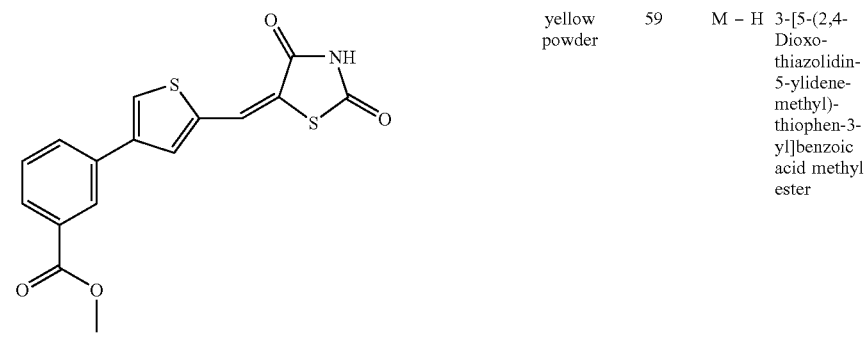  Compound F16 | yellow powder | 59 | M − H | 3-[5-(2,4-Dioxo-thiazolidin-5-ylidene-methyl)-thiophen-3-yl]benzoic acid methyl ester |
|   Compound F17 | yellow flakes | 71 | M − H | 5-(5-Phenyl-furan-2-yl-methylene)-thiazolidine-2,4-dione |

-continued

| | Appearance | LC purity | MS | Name |
|---|---|---|---|---|
| 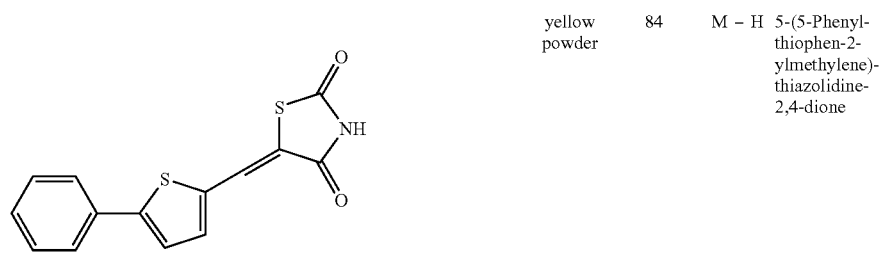   Compound F18 | yellow powder | 84 | M − H | 5-(5-Phenyl-thiophen-2-ylmethylene)-thiazolidine-2,4-dione |

| Heterocyclic structure G | Appearance | LC purity | MS | Name |
|---|---|---|---|---|
| 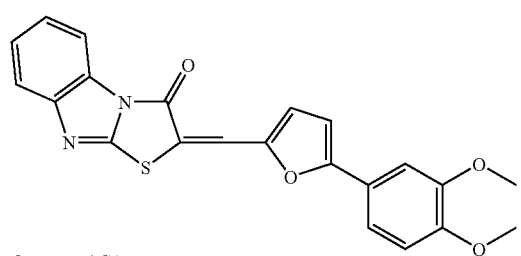   Compound G1 | orange powder | 62 | M + H | 2-[5-(3,4-Dimethoxy-phenyl)furan-2-yl-methylene]-benzo[4,5]-imidazo[2,1-b]thiazol-3-one |

*LC: Liquid chromatography
**MS: Mass spectrometry

The compounds according to the invention can be synthesized according to the process described below.

General Procedure for the Synthesis of the Compounds with the D, E, F or G Structure:

These heterocyclic structures correspond respectively to 3-ethyl-2-thioxo-4-oxazolidinone (CAS number: 10574-66-0, molar mass: 145, structure D), to 2-thiohydantoin (CAS number: 503-87-7, molar mass: 116, structure E), to 2,4-thiazolidinedione (CAS number: 2295-31-0, molar mass: 117, structure F) and to thiazolo[2,3-b]benzimidazole-3 (2H)-one (CAS number: 3042-01-1, molar mass: 190, structure G).

100 mg of aldehyde, 1 equivalent of hetero-cycle of structure D, E, F or G, 20 μl of piperidine and then 1.5 ml of absolute ethanol are introduced into a Pyrex® reaction tube of the synthesis system under Discover microwave irradiation from STEM.

The tube is equipped with a magnetic bar and then closed by a crimped stopper.

The reaction medium is subsequently irradiated in the Discover device according to the following parameters:
Power released: 250 W
Set temperature: 150° C.
Irradiation time: 2 minutes
Maximum time to reach the set-point: 4 minutes.

After cooling, the reaction medium is filtered through a sintered glass filter and the solid is washed with the minimum amount of absolute ethanol and then dried under vacuum.

Yield: 40-100%

The samples are analysed by LC-UV-MS according to the following conditions:

Gradient: acetonitrile 10/water 90 to acetonitrile 90/water 10 in 8 minutes
Column: X-terra_MS C18 3.5 μm 3×50 mm
Flow rate: 0.5 ml/min
UV: linear array of 290 nm-450 nm diodes
MS: Electrospray with ionization at positive and negative atmospheric pressure.

The reaction scheme of Compounds 1, 3, 4 and 8 is given below by way of example.

Example 1

Compound 1

Preparation of 4-{5-[(2,4-dioxo-1,3-thiazolidin-5-ylidene)methyl]-2-furyl}benzoic acid Reaction scheme

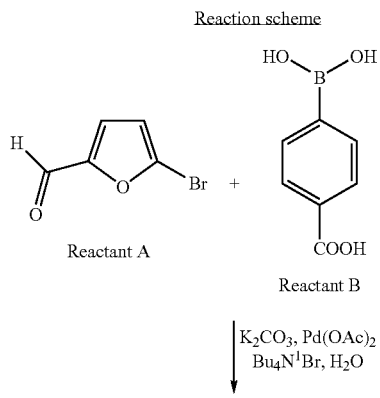

Reactant A           Reactant B

K$_2$CO$_3$, Pd(OAc)$_2$
Bu$_4$N$^I$Br, H$_2$O

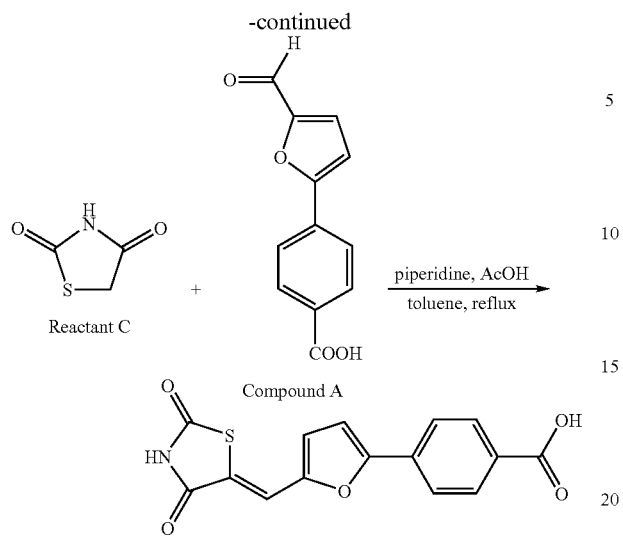

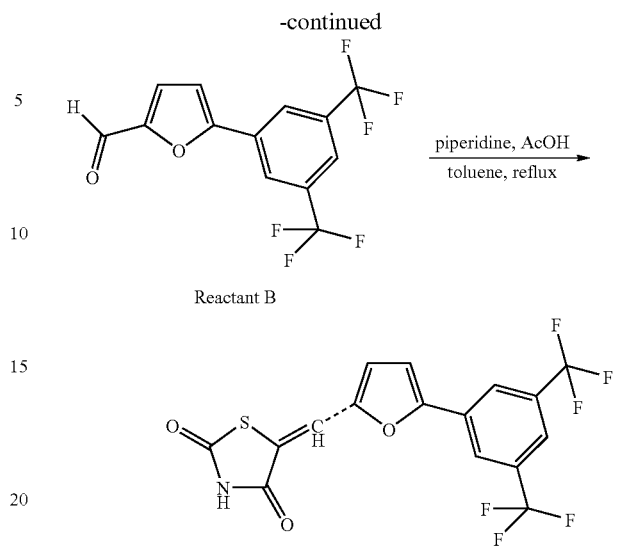

Procedure

Stage 1

1.99 g (6.16 mmol) of tetrabutylammonium bromide are dissolved in 100 ml of water in a 50 ml three-necked round-bottomed flask equipped with a cooling system and a magnetic stirrer and then 1.12 g (6.7 mmol) of 4-carboxyphenylboronic acid (reactant B), 1.08 g (6.16 mmol) of 5-bromo-2-furaldehyde (reactant A), 30 mg (2 mol %) of palladium acetate and 2.12 g (15.4 mmol) of potassium carbonate are introduced. The reaction medium is left at ambient temperature (20-25° C.) for 12 hours. The mixture is subsequently washed with ethyl acetate (3 times with 50 ml). The aqueous phase is acidified to pH=1-2 with a 35% hydrochloric acid solution. The yellow-beige solid formed (compound A) is filtered off, then rinsed with water (3 times with 20 ml) and dried under vacuum in the presence of 1.2 g of phosphorus pentoxide. The reaction yield is 90%.

Stage 2

0.38 g (3.25 mmol) of thiazolidin-2,4-dione is dissolved in 20 ml of toluene in a 50 ml three-necked round-bottomed flask equipped with a Dean and Stark apparatus, a thermometer and a magnetic stirrer and then 0.7 g (3.25 mmol) of yellow-beige solid formed above (compound A) is introduced. 0.15 ml of acetic acid and 0.15 ml of piperidine are subsequently added and then the mixture is brought to reflux for 5 hours. A yellow solid is formed and is filtered off and then rinsed with toluene (2 times with 20 ml). The product is then dried under vacuum in the presence of 0.85 g of phosphorus pentoxide. The crude reaction yield is 78%.

Analysis

Nuclear Magnetic Resonance: The spectrum obtained is in agreement with the structure proposed.

Example 2

Compound 3

Preparation of 5-({5-[3,5-bis(trifluoromethyl)phenyl]-2-furyl}methylene)-1,3-thiazolidine-2,4-dione Reaction scheme

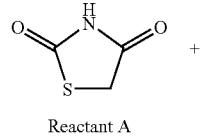

Reactant A

Procedure 0.38 g (3.25 mmol) of thiazolidin-2,4-dione (reactant A) is dissolved in 20 ml of toluene in a 50 ml three-necked round-bottomed flask equipped with a Dean and Stark apparatus, a thermometer and a magnetic stirrer and then 1 g (3.25 mmol) of 5-[3,5-bis(trifluoromethyl)phenyl]-2-furaldehyde (reactant B) is introduced. 0.15 ml of acetic acid (AcOH) and 0.15 ml of piperidine are subsequently added and then the mixture is brought to reflux for 5 hours. A yellow solid was formed during the reaction. It is filtered off, then rinsed with toluene (2 times with 20 ml) and dried under vacuum in the presence of 0.86 g of phosphorus pentoxide. The reaction yield is 65%.

Analysis

Mass spectrometry: The quasimolecular ion (M–H)— of the expected molecule, $C_{16}H_7F_6NO_3S$, is mainly detected.

Nuclear Magnetic Resonance: The spectrum obtained is in agreement with the structure proposed.

Example 3

Compound 4

Preparation of 3-{5-[(2,4-dioxo-1,3-thiazolidin-5-ylidene)methyl]-2-furyl}benzoic acid Reaction scheme

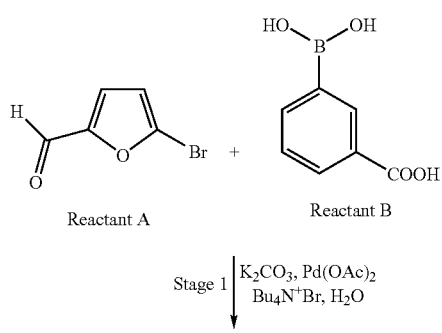

Stage 1 | $K_2CO_3$, $Pd(OAc)_2$
$Bu_4N^+Br^-$, $H_2O$

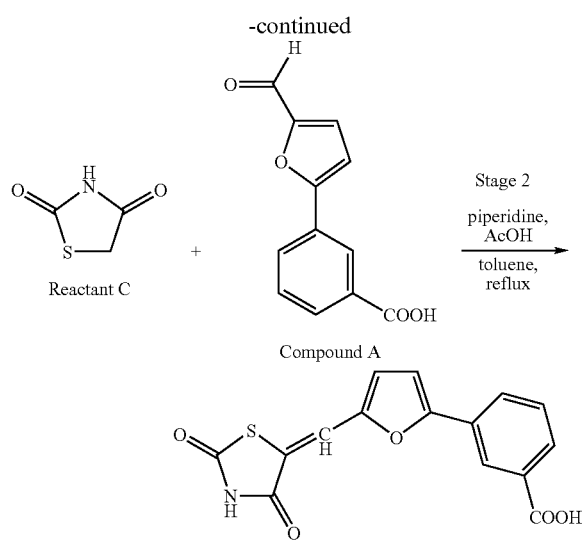

Procedure

Stage 1

1.99 g (6.16 mmol) of tetrabutylammonium bromide are dissolved in 100 ml of water in a 50 ml three-necked round-bottomed flask equipped with a cooling system and a magnetic stirrer and then 1.12 g (6.7 mmol) of 3-carboxyphenylboronic acid (reactant B), 1.08 g (6.16 mmol) of 5-bromo-2-furaldehyde (reactant A), 30 mg (2 mol %) of palladium acetate and 2.12 g (15.4 mmol) of potassium carbonate are introduced. The reaction medium is left at ambient temperature (20-25° C.) for 12 hours. The mixture is subsequently washed with ethyl acetate (3 times with 50 ml). The aqueous phase is acidified to pH=1-2 with an aqueous hydrochloric acid solution: 35%. The pinkish-beige solid formed (compound A) is filtered off, then rinsed with water (3 times with 20 ml) and dried under vacuum in the presence of 1.1 g of phosphorus pentoxide. The reaction yield obtained is 82%.

Stage 2

0.542 g (4.62 mmol) of thiazolidin-2,4-dione is dissolved in 20 ml of toluene in a 50 ml three-necked round-bottomed flask equipped with a Dean and Stark apparatus, a thermometer and a magnetic stirrer and then 1 g (4.62 mmol) of the pinkish-beige solid formed above (compound A) is introduced. 0.15 ml of acetic acid (AcOH) and 0.15 ml of piperidine are subsequently added and then the mixture is brought to reflux for 5 hours. The formation of a yellow solid is observed, which solid is filtered off and then rinsed with toluene (2 times with 20 ml). The solid is subsequently dispersed in 100 ml of water. A 2N aqueous sodium hydroxide solution is then added until the product has completely dissolved and then acidification is carried out with a 1N aqueous hydrochloric acid solution until a pH of 1-2 is reached. The brown solid formed is filtered off, then washed with water (2 times with 50 ml) and dried under vacuum in the presence of 0.86 g of phosphorus pentoxide. The yield is 63%.

Analysis

Nuclear Magnetic Resonance: The spectrum obtained is in agreement with the structure proposed.

Example 4

Compound 8

Preparation of the disodium salt of 3-{5-[(2,4-dioxo-1,3-thiazolidin-5-ylidene)methyl]-2-furyl}benzoic acid Reaction scheme

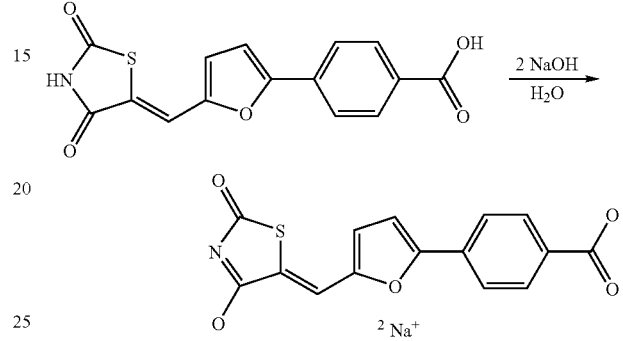

Procedure 15 g of 3-{5-[(2,4-dioxo-1,3-thiazolidin-5-ylidene)methyl]-2-furyl}benzoic acid are dissolved in 500 ml of an aqueous sodium hydroxide solution (2 equivalents). This solution is washed with 2 times 50 ml of dichloromethane and then partially concentrated. This solution is then run onto acetone. 11 g of an orange-yellow precipitate, corresponding to the disodium salt of 3-{5-[(2,4-dioxo-1,3-thiazolidin-5-ylidene)methyl]-2-furyl}benzoic acid, in the Z form, are thus obtained.

Analysis

Nuclear Magnetic Resonance: The spectrum obtained is in agreement with the structure proposed.

Example 5

Demonstration of the Specific Inhibitory Properties with Respect to 15-PGDH of the Compounds of formula (I)

1) Test on 15-PGDH

The enzyme 15-PGDH is obtained as disclosed in Application FR-A-02/05067, filed on behalf of L'Oréal, in suspension in a suitable medium at a concentration of 0.3 mg/ml, then blocked at −80° C. For the requirements of the test, this suspension is defrosted and stored in ice.

Furthermore, a Tris 100 mM, pH=7.4, buffer comprising 0.1 mM of dithiothreitol (D5545, Sigma-Aldrich, L'isle D'Abeau Chesne, BP 701, 38297, Saint Quentin Fallavier), 1.5 mM of β-NAD (N6522, Sigma-Aldrich, L'isle D'Abeau Chesne, BP 701, 38297, Saint Quentin Fallavier) and 50 μM of prostaglandin $E_2$ (P4172, Sigma-Aldrich, L'isle D'Abeau Chesne, BP 701, 38297, Saint Quentin Fallavier) is prepared.

0.965 ml of this buffer (brought beforehand to 37° C.) is introduced into the cell of a spectrophotometer (Perkin-Elmer, Lambda 2) thermostatically controlled at 37° C., the wavelength of which for the measurement is adjusted to 340 nm. 0.035 ml of enzymatic suspension at 37° C. is introduced into the cell concomitantly with the recording (corresponding to an increase in optical density at 340 nm). The maximum rate of reaction is noted.

The test values (comprising the compounds (I)) are compared with the control value (without compound (I)); the results indicated represent the concentration at which the compound (I) inhibits 50% of the enzymatic activity of 15-PGDH, referred to as $IC_{50}dh$.

2) Test on PGFS

The enzyme PGF synthase is obtained as disclosed in the document FR-A-02/05067, at a concentration of 0.5 mg/ml, in suspension in an appropriate medium, and is blocked at −80° C. For the requirements of the test, this suspension is defrosted and stored in ice.

Furthermore, a Tris 100 mM, pH=6.5, buffer comprising 20 μM of 9,10-phenanthrenequinone* (P2896, Sigma-Aldrich, L'isle D'Abeau Chesne, BP 701, 38297, Saint Quentin Fallavier) and 100 μM of β-NADPH(N1630, Sigma-Aldrich, L'isle D'Abeau Chesne, BP 701, 38297, Saint Quentin Fallavier) is prepared in a brown bottle (exclusion of light).

* A mother solution assaying 1 mM is prepared in absolute ethanol and is brought to 40° C.; the bottle is placed in an ultrasonic bath to facilitate the dissolution of the product.

0.950 ml of this buffer (brought beforehand to 37° C.) is introduced into the cell of a spectrophotometer (Perkin-Elmer, Lambda 2) thermostatically controlled at 37° C., the wavelength of which for the measurement is adjusted to 340 nm. 0.05 ml of enzymatic suspension at 37° C. is introduced into the cell concomitantly with the recording (corresponding to a fall in optical density at 340 nm). The maximum rate of reaction is noted.

The test values (comprising the compound (I)) are compared with the control value (without compound (I)); the results indicated represent the concentration at which the compound (I) inhibits the enzymatic activity of PGFS by 50%, referred to as $IC_{50}fs$.

It emerges from this table that the ratio $IC_{50}fs/IC_{50}dh$ of Compound 1 is greater than 13. Compound 1 therefore clearly has an inhibitory activity with respect to 15-PGDH and in particular an activity which is selective with respect to PGFS.

The compositions below are obtained by the usual techniques commonly used in the cosmetic or pharmaceutical field.

Example 6

Hair Lotion

| | |
|---|---:|
| Compound 1 | 0.80 g |
| Propylene glycol | 10.00 g |
| Isopropyl alcohol | q.s. for 100.00 g |

This lotion is applied to the scalp one or two times daily at the rate of 1 ml per application, the scalp being lightly massaged to bring about the penetration of the active principle. The hair is subsequently dried in the open air. This lotion makes it possible to reduce hair loss and to promote hair regrowth.

Example 7

Hair Lotion

| | |
|---|---:|
| Compound 2 | 1.00 g |
| Propylene glycol | 30.00 g |
| Ethyl alcohol | 40.00 g |
| Water | q.s. for 100.00 g |

This lotion is applied to the scalp one or two times daily at the rate of 1 ml per application, the scalp being lightly massaged to bring about the penetration of the active principle. The hair is subsequently dried in the open air.

| Compound | Structure | Inhibition of 15-PGDH $IC_{50}dh$ (μM) | Inhibition of PGFS $IC_{50}fs$ (μM) |
|---|---|---|---|
| 1 | 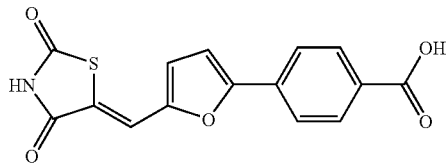 | 0.3 | 4 |

Example 8

Hair Lotion

| | |
|---|---:|
| Compound 1 | 1 g |
| Ethyl alcohol | 40.00 g |
| NaOH | q.s. for (*) |
| Water | q.s. for 100.00 g |

(*) amount sufficient to neutralize the acid functional group carried by the phenyl ring ($R_1$)

This lotion is applied to the scalp one or two times daily at the rate of 1 ml per application, the scalp being lightly massaged to bring about the penetration of the active principle.

Example 9

Demonstration of the Specific Inhibitory Effectiveness for 15PGDH on a Cell Model The present study is targeted at evaluating the compounds of formula (I) in a cell model. This study makes it possible to determine the penetration of the active principle into the cytosol and its effectiveness as specific inhibitor of 15-PGDH under more complex experimental conditions than a simple reaction medium.

Equipment and Methods

D-2. Culturing of U937 (CRL-1593 American Type Cells Collection) in RPMI medium 1640+10% of foetal calf serum+2 mM of L-glutamine+antibiotics at 37° C. under 5% of $CO_2$.

D-1. Preparation of a suspension of U937 ($1 \times 10^6$ cells/ml) in RPMI medium 1640+10% of foetal calf serum+2 mM of glutamine+antibiotics+10 nM of PMA (phorbol 12-myristate 13-acetate); introduction of 200 μl per test well of this suspension into a 96-well plate (3 wells per molecule and per concentration to be tested+corresponding controls); incubation at 37° C. for 36 h 00 under 5% $CO_2$.

D0. Removal of the supernatants (the cells have adhered to the bottom of the wells: monitoring using a microscope) and introduction into each well of 100 μl of RPMI 1640+2 mM of L-glutamine+10 ng of LipoPolySaccharide (LPS) (except absolute control)+the test molecule at the desired concentration (in this instance, 5 and 25 μM).

Incubation at 37° C. for 6 h 00 under 5% of $CO_2$.

The mother solutions of test molecules are at 25 mM in DiMethyl SulfOxide.

All the wells comprise the same final amount of DMSO. Immediate evaluation of the amount of $PGF_2$, secreted by the cells (50 μl) under the various conditions (molecules or controls) by the use of an immuno-enzymatic assay kit (Cayman, Ref. 516011).

| Results below as % of the LPS control. | |
|---|---|
| Reference Molecule (5 μM) | % of the control |
| Compound 1: | +76 ± 20 |
| Compound 8: | +44 ± 16 |

This confirms that the compounds according to the invention are selective inhibitors of 15-PGDH in a cell environment and protect prostaglandins.

Example 10

Hair Lotion

| | |
|---|---:|
| Compound 8 | 1 g |
| Ethyl alcohol | 40.00 g |
| Propylene glycol | 30.00 g |
| Water | q.s. for 100.00 g |

Example 11

Wax/Water Mascara

| | |
|---|---:|
| Beeswax | 6.00% |
| Paraffin wax | 13.00% |
| Hydrogenated jojoba oil | 2.00% |
| Water-soluble film-forming polymer | 3.00% |
| Triethanolamine stearate | 8.00% |
| Compound 5 | 1.00% |
| Black pigment | 5.00% |
| Preservative | q.s. |
| Water | q.s. for 100.00% |

This mascara is applied to the eyelashes like a conventional mascara with a mascara brush.

Example 12

Hair Lotion

| | |
|---|---:|
| Compound 8 | 0.10 g |
| Latanoprost | 0.10 g |
| Propylene glycol | 30.00 g |
| Ethyl alcohol | 40.00 g |
| Water | q.s. for 100.00 g |

Example 13

Hair Lotion

| | |
|---|---:|
| Compound 8 | 1% |
| Ethyl alcohol | 49.5% |
| Water | q.s. for 100% |

This lotion is applied to the scalp one or two times daily at the rate of 1 ml per application, the scalp being lightly massaged to bring about the penetration of the active principle. The hair is subsequently dried in the open air. This lotion makes it possible to reduce hair loss and to promote hair regrowth. It also makes it possible to improve the appearance of the hair.

The invention claimed is:

1. A method of inducing the growth of keratinous fibers, or stimulating the growth of keratinous fibers, or slowing the loss of keratinous fibers or increasing the density of keratinous fibers in a subject in need of same; said method comprising applying to said subject a composition comprising an effective amount of at least one heterocyclic compound of formula (I) or of one of its salts,

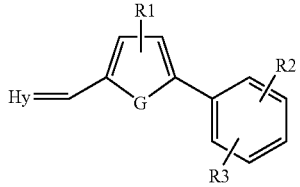

in which:

Hy represents a heterocycle of formula (II):

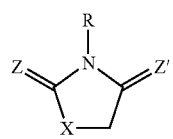

where Z and Z' independently represent S or O, X independently represents S or O or NH, R denotes a hydrogen, a linear or branched $C_1$-$C_{20}$ alkyl radical or an aryl radical;

G represents O, S or NH;

$R_1$, $R_2$ and $R_3$ represent, independently of one another, a hydrogen, a halogen, an $OR_0$, $SR_0$, $NR_0R_0'$, $COR_0$, $CSR_0$, $NR_0CONR_0'R_0''$, $C(=NR_0)R_0'$, $C(=NR_0)NR_0'R_0''$, $NR_0C(=NR_0')NR_0''R_0'''$, $OCOR_0$, $COSR_0$, $SCOR_0$, $CSNR_0R_0'$, $NR_0CSR_0'$, $NR_0CSNR_0'R_0''$, $COOR_0$, $CONR_0R_0'$, $CF_3$, $NO_2$, $CN$, $NR_0COR_0'$, $SO_2R_0'$, $SO_2NR_0R_0'$ or $NR_0SO_2R_0'$ group, a saturated linear or branched $C_1$-$C_{20}$ alkyl radical, an unsaturated linear or branched $C_1$-$C_{20}$ alkyl radical, or at least one saturated or unsaturated ring of 4 to 7 atoms, wherein the rings are separate or fused, where $R_0$, $R_0'$, $R_0''$ and $R_0'''$, which are identical or different, denote a hydrogen, a linear or branched $C_1$-$C_{20}$ alkyl radical or an aryl radical.

2. A method of caring for human keratinous fibers, or inducing and/or stimulating the growth of human keratinous fibers, or slowing the loss of human keratinous fibers and/or increasing the density of human keratinous fibers and/or treating androgenic alopecia in a subject in need of same; said method comprising applying to said subject a composition comprising an effective amount of at least one heterocyclic compound of formula (I) or of one of its salts,

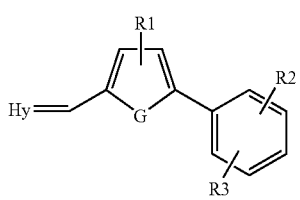

in which:

Hy represents a heterocycle of formula (II):

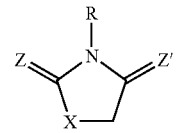

where Z and Z' independently represent S or O, X independently represents S or O or NH, R denotes a hydrogen, a linear or branched $C_1$-$C_{20}$ alkyl radical or an aryl radical;

G represents O, S or NH;

$R_1$, $R_2$ and $R_3$ represent, independently of one another, a hydrogen, a halogen, an $OR_0$, $SR_0$, $NR_0R_0'$, $COR_0$, $CSR_0$, $NR_0CONR_0'R_0''$, $C(=NR_0)R_0'$, $C(=NR_0)NR_0'R_0''$, $NR_0C(=NR_0')NR_0''R_0'''$, $OCOR_0$, $COSR_0$, $SCOR_0$, $CSNR_0R_0'$, $NR_0CSR_0'$, $NR_0CSNR_0'R_0''$, $COOR_0$, $CONR_0R_0'$, $CF_3$, $NO_2$, $CN$, $NR_0COR_0'$, $SO_2R_0'$, $SO_2NR_0R_0'$ or $NR_0SO_2R_0'$ group, a saturated linear or branched $C_1$-$C_{20}$ alkyl radical, an unsaturated linear or branched $C_1$-$C_{20}$ alkyl radical, or at least one saturated or unsaturated ring of 4 to 7 atoms, wherein the rings are separate or fused, where $R_0$, $R_0'$, $R_0''$ and $R_0'''$, which are identical or different, denote a hydrogen, a linear or branched $C_1$-$C_{20}$ alkyl radical or an aryl radical.

3. A method of inhibiting 15-hydroxyprostaglandin dehydrogenase and thus maintaining and/or increasing the density of human keratinous fibers in a subject in need of same, said method comprising applying to said subject a composition comprising an effective amount of at least one heterocyclic compound of formula (I) or of one of its salts,

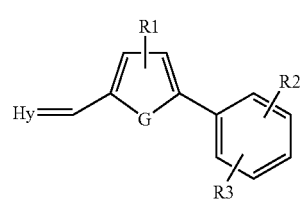

in which:

Hy represents a heterocycle of formula (II):

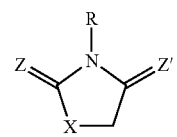

where Z and Z' independently represent S or O, X independently represents S or O or NH, R denotes a hydrogen, a linear or branched $C_1$-$C_{20}$ alkyl radical or an aryl radical;

G represents O, S or NH;

$R_1$, $R_2$ and $R_3$ represent, independently of one another, a hydrogen, a halogen, an $OR_0$, $SR_0$, $NR_0R_0'$, $COR_0$, $CSR_0$, $NR_0CONR_0'R_0''$, $C(=NR_0)R_0'$, $C(=NR_0)$ $NR_0'R_0''$, $NR_0C(=NR_0')NR_0''R_0'''$, $OCOR_0$, $COSR_0$, $SCOR_0$, $CSNR_0R_0'$, $NR_0CSR_0'$, $NR_0CSNR_0'R_0''$, $COOR_0$, $CONR_0R_0'$, $CF_3$, $NO_2$, $CN$, $NR_0COR_0'$, $SO_2R_0'$, $SO_2NR_0R_0'$ or $NR_0SO_2R_0'$ group, a saturated linear or branched $C_1$-$C_{20}$ alkyl radical, an unsaturated linear or branched $C_1$-$C_{20}$ alkyl radical, or at least one saturated or unsaturated ring of 4 to 7 atoms wherein the rings are separate or fused, where $R_0$, $R_0'$, $R_0''$ and $R_0'''$, which are identical or different, denote a hydrogen, a linear or branched $C_1$-$C_{20}$ alkyl radical or an aryl radical.

4. The method of claim 1, wherein the keratinous fibers are the hair, eyebrows, eyelashes, beard hairs, moustache hairs and pubic hairs.

5. A method of reducing hair loss and/or increasing hair density and/or treating androchronogenetic alopecia and/or treating alopecia of natural origin in a subject in need of same; said method comprising applying to said subject a cosmetic or pharmaceutical composition comprising an effective amount of at least one heterocyclic compound of formula (I) or of one of its salts,

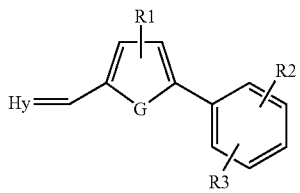

(I)

in which:

Hy represents a heterocycle of formula (II):

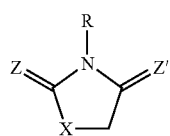

(II)

where Z and Z' independently represent S or O, X independently represents S or O or NH, R denotes a hydrogen, a linear or branched $C_1$-$C_{20}$ alkyl radical or an aryl radical;

G represents O, S or NH;

$R_1$, $R_2$ and $R_3$ represent, independently of one another, a hydrogen, a halogen, an $OR_0$, $SR_0$, $NR_0R_0'$, $COR_0$, $CSR_0$, $NR_0CONR_0'R_0''$, $C(=NR_0)R_0'$, $C(=NR_0)NR_0'R_0''$, $NR_0C(=NR_0')NR_0''R_0'''$, $OCOR_0$, $COSR_0$, $SCOR_0$, $CSNR_0R_0'$, $NR_0CSR_0'$, $NR_0CSNR_0'R_0''$, $COOR_0$, $CONR_0R_0'$, $CF_3$, $NO_2$, $CN$, $NR_0COR_0'$, $SO_2R_0'$, $SO_2NR_0R_0'$ or $NR_0SO_2R_0'$ group, a saturated linear or branched least one saturated or unsaturated ring of 4 to 7 atoms wherein the rings are separate or fused, where $R_0$, $R_0'$, $R_0''$ and $R_0'''$, which are identical or different, denote a hydrogen, a linear or branched $C_1$-$C_{20}$ alkyl radical or an aryl radical.

6. A method of inducing and/or stimulating the growth of eyelashes and/or increasing the density of eyelashes in a subject in need of same; said method comprising applying to said subject a cosmetic composition comprising an effective amount at least one heterocyclic compound of formula (I) or of one of its salts,

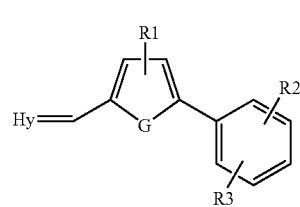

(I)

in which:

Hy represents a heterocycle of formula (II):

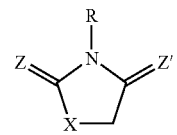

(II)

where Z and Z' independently represent S or O, X independently represents S or O or NH, R denotes a hydrogen, a linear or branched $C_1$-$C_{20}$ alkyl radical or an aryl radical;

G represents O, S or NH;

$R_1$, $R_2$ and $R_3$ represent, independently of one another, a hydrogen, a halogen, an $OR_0$, $SR_0$, $NR_0R_0'$, $COR_0$, $CSR_0$, $NR_0CONR_0'R_0''$, $C(=NR_0)R_0'$, $C(=NR_0)NR_0'R_0''$, $NR_0C(=NR_0')NR_0''R_0'''$, $OCOR_0$, $COSR_0$, $SCOR_0$, $CSNR_0R_0'$, $NR_0CSR_0'$, $NR_0CSNR_0'R_0''$, $COOR_0$, $CONR_0R_0'$, $CF_3$, $NO_2$, $CN$, $NR_0COR_0'$, $SO_2R_0'$, $SO_2NR_0R_0'$ or $NR_0SO_2R_0'$ group, a saturated linear or branched $C_1$-$C_{20}$ alkyl radical, an unsaturated linear or branched $C_1$-$C_{20}$ alkyl radical, or at least one saturated or unsaturated ring of 4 to 7 atoms, wherein the rings are separate or fused, where $R_0$, $R_0'$, $R_0''$ and $R_0'''$, which are identical or different, denote a hydrogen, a linear or branched $C_1$-$C_{20}$ alkyl radical or an aryl radical.

7. The method of claim 1, wherein in the compound of formula (I), $R_2$ and $R_3$ are in the para- and meta-position respectively, with regard to the following part A:

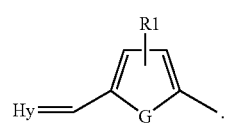

(A)

8. The method of claim 1, wherein in the compound of formula (I), $R_1$ represents a hydrogen atom.

9. The method of claim 1, wherein in the compound of formula (I), at least one of the $R_2$ and $R_3$ groups represents $CF_3$, $OR_0$ or $COOR_0$ with $R_0$ being H or a linear or branched, $C_1$-$C_{20}$ alkyl radical.

10. The method of claim 9, wherein in the compound of formula (I), $COOR_0$ represents COOH or COOCH$_2$—CH$_3$.

11. The method of claim 1, wherein in the compound of formula (I), $R_2$ represents COOH and $R_3$ represents H; $R_2$ represents COOH$_2$—CH$_3$ and $R_3$ represents H; or $R_2$ and $R_3$ represent $CF_3$ or $OCH_3$.

12. The method of claim 1, wherein the compound of formula (I) comprises one or two carbonyl groups, wherein the carbon of the carbonyl group forms part of the heterocycle.

13. The method of claim 1 wherein the heterocyclic compound of formula (I) exhibits the following formula (IIIa) or the corresponding salt form:

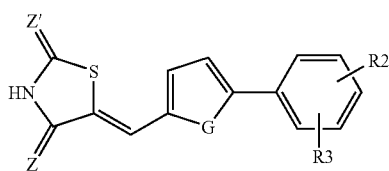

(IIIa)

in which Z, Z' and G independently represent O or S; and at least one of the $R_2$ and $R_3$ groups represents $CF_3$, $OR_0$ or $COOR_0$ with $R_0$ being H or a linear or branched, $C_1$-$C_{20}$ alkyl radical.

14. The method of claim 1 wherein the compound of formula (I) comprises a thiazolidinedione ring.

15. The method of claim 13, wherein, when Z=Z'=G, at least one of the $R_2$ and $R_3$ groups represents $CF_3$ or $COOR_0$ with $R_0$ being a saturated, linear or branched, $C_1$-$C_{10}$ alkyl radical.

16. The method of claim 1, wherein the salt of the compound of formula (I) is a salt selected from the group consisting of sodium salts, potassium salts, salts of zinc ($Zn^{2+}$), of calcium ($Ca^{2+}$), of copper ($Cu^{2+}$), of Iron ($Fe^{2+}$), of strontium ($Sr^{2+}$), of magnesium ($Mg^{2+}$) of mangnesium ($Mn^{2+}$), of ammonium, triethanolamine, monoethanolamine, diethanolamine, hexadecylamine, N,N,N',N'-tetrakis(2-hydroxypropyl)ethylenediamine, tris(hydroxymethyl)aminomethane salts, hydroxides, carbonates, halides, sulphates, phosphates and nitrates.

17. The method of claim 1, wherein the compound of formula (I) is selected from the group consisting of:

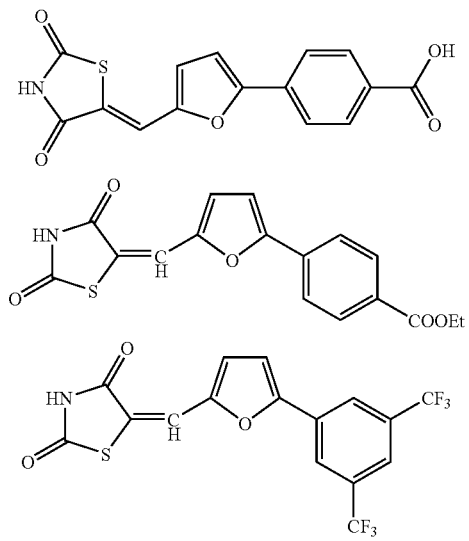

-continued

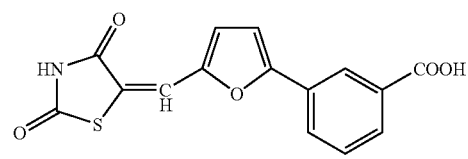

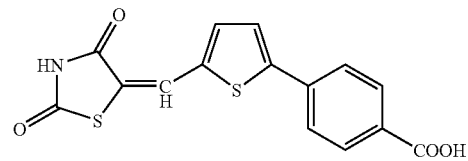

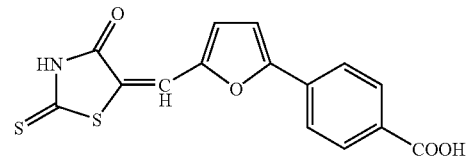

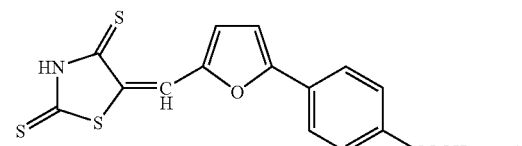

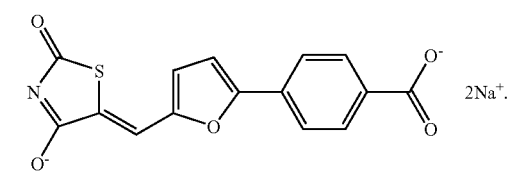

18. The method of claim 1 wherein the compound of formula (I) or a mixture of compounds of formula (I) is used at a concentration ranging from $10^3$ to 10% with respect to the total weight of the composition.

19. The method of claim 1, wherein the composition is applied topically.

20. A method for the cosmetic treatment of keratinous fibers and/or of the skin from where the said fibers emerge in a subject in need of same, said method comprising applying, to the fibers and/or the skin of said subject, a composition as defined in claim 1, leaving this composition in contact with the fibers and/or the skin and optionally rinsing, wherein the composition is a cosmetic composition.

21. A method for improving the condition and/or appearance of human eyelashes in a subject in need of same, said method comprising applying to the eyelashes and/or eyelids of said subject a mascara composition comprising at least one compound of formula (I) or one of its salts,

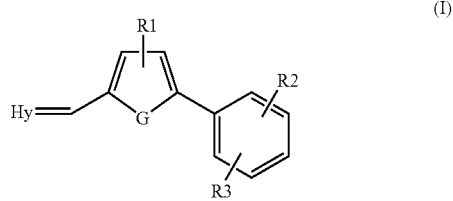

(I)

in which:

Hy represents a heterocycle of formula (II):

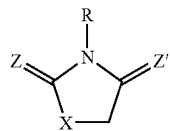

where Z and Z' independently represent S or O, X independently represents S or O or NH, R denotes a hydrogen, a linear or branched $C_1$-$C_{20}$ alkyl radical or an aryl radical;

G represents O, S or NH;

$R_1$, $R_2$ and $R_3$ represent, independently of one another, a hydrogen, a halogen, an $OR_0$, $SR_0$, $NR_0R_0'$, $COR_0$, $CSR_0$, $NR_0CONR_0'R_0''$, $C(=NR_0)R_0'$, $C(=NR_0)NR_0'R_0''$, $NR_0C(=NR_0')NR_0''R_0'''$, $OCOR_0$, $COSR_0$, $SCOR_0$, $CSNR_0R_0'$, $NR_0CSR_0'$, $NR_0CSNR_0'R_0''$, $COOR_0$, $CONR_0R_0'$, $CF_3$, $NO_2$, $CN$, $NR_0COR_0'$, $SO_2R_0'$, $SO_2NR_0R_0'$ or $NR_0SO_2R_0'$ group, a saturated linear or branched $C_1$-$C_{20}$ alkyl radical, an unsaturated linear or branched $C_1$-$C_{20}$ alkyl radical, or at least one saturated or unsaturated ring of 4 to 7 atoms, wherein the rings are separate or fused, where $R_0$, $R_0'$, $R_0''$ and $R_0'''$, which are identical or different, denote a hydrogen, a linear or branched $C_1$-$C_{20}$ alkyl radical or an aryl radical, and leaving this composition in contact with the eyelashes and/or eyelids.

22. A method for improving the condition and/or appearance of human scalp in a subject in need of same, said method comprising applying to the hair and/or the scalp of said subject a cosmetic composition comprising an effective amount of at least one compound of formula (I) or one of its salts,

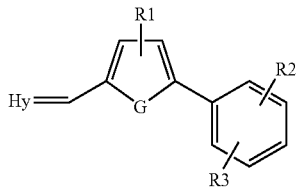

in which:

Hy represents a heterocycle with of formula (II):

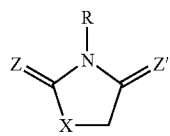

where Z and Z' independently represent S or O, X independently represents S or O or NH, R denotes a hydrogen, a linear or branched $C_1$-$C_{20}$ alkyl radical or an aryl radical;

G represents O, S or NH;

$R_1$, $R_2$ and $R_3$ represent, independently of one another, a hydrogen, a halogen, an $OR_0$, $SR_0$, $NR_0R_0'$, $COR_0$, $CSR_0$, $NR_0CONR_0'R_0''$, $C(=NR_0)R_0'$, $C(=NR_0)NR_0'R_0''$, $NR_0C(=NR_0')NR_0''R_0'''$, $OCOR_0$, $COSR_0$, $SCOR_0$, $CSNR_0R_0'$, $NR_0CSR_0'$, $NR_0CSNR_0'R_0''$, $COOR_0$, $CONR_0R_0'$, $CF_3$, $NO_2$, $CN$, $NR_0COR_0'$, $SO_2R_0'$, $SO_2NR_0R_0'$ or $NR_0SO_2R_0'$ group, a saturated linear or branched $C_1$-$C_{20}$ alkyl radical, an unsaturated linear or branched $C_1$-$C_{20}$ alkyl radical, or at least one saturated or unsaturated ring of 4 to 7 atoms, wherein the rings are separate or fused, where $R_0$, $R_0'$, $R_0''$ and $R_0'''$, which are identical or different, denote a hydrogen, a linear or branched $C_1$-$C_{20}$ alkyl radical or an aryl radical, and leaving this composition in contact with the hair and/or the scalp and optionally rinsing the hair and/or the scalp.

23. A method of preserving the amount and/or the activity of prostaglandins in the hair follicle in a subject in need of same, said method comprising applying to the skin and/or hair of said subject a cosmetic composition comprising an effective amount of at least one heterocyclic compound of formula (I) or of one of its salts,

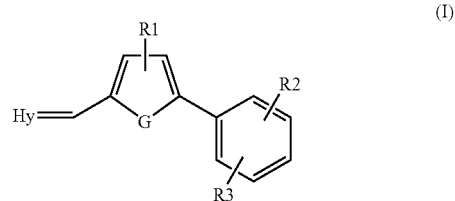

in which:

Hy represents a heterocycle with of formula (II):

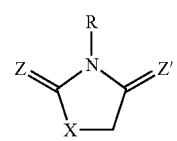

where Z and Z' independently represent S or O, X independently represents S or O or NH, R denotes a hydrogen, a linear or branched $C_1$-$C_{20}$ alkyl radical or an aryl radical;

G represents O, S or NH;

$R_1$, $R_2$ and $R_3$ represent, independently of one another, a hydrogen, a halogen, an $OR_0$, $SR_0$, $NR_0R_0'$, $COR_0$, $CSR_0$, $NR_0CONR_0'R_0''$, $C(=NR_0)R_0'$, $C(=NR_0)NR_0'R_0''$, $NR_0C(=NR_0')NR_0''R_0'''$, $OCOR_0$, $COSR_0$, $SCOR_0$, $CSNR_0R_0'$, $NR_0CSR_0'$, $NR_0CSNR_0'R_0''$, $COOR_0$, $CONR_0R_0'$, $CF_3$, $NO_2$, $CN$, $NR_0COR_0'$, $SO_2R_0'$, $SO_2NR_0R_0'$ or $NR_0SO_2R_0'$ group, a saturated linear or branched $C_1$-$C_{20}$ alkyl radical, an unsaturated linear or branched $C_1$-$C_{20}$ alkyl radical, or at least one saturated or unsaturated ring of 4 to 7 atoms, wherein the rings are separate or fused, where $R_0$, $R_0'$, $R_0''$ and $R_0'''$, which are identical or different, denote a hydrogen, a linear or branched $C_1$-$C_{20}$ alkyl radical or an aryl radical.

24. The method of claim 1, wherein in the compound of formula (I), at least one of the $R_2$ and $R_3$ groups represents $CF_3$, $OR_0$ or $COOR_0$ with $R_0$ being H or a linear or branched, $C_1$-$C_{10}$ alkyl radical.

25. The method of claim 1 wherein the heterocyclic compound of formula (I) exhibits the following formula (IIIa) or the corresponding salt form:

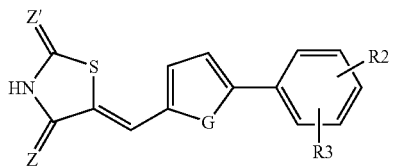

(IIIa)

in which Z and Z' independently represent O or S and G represents O; and at least one of the $R_2$ and $R_3$ groups represents $CF_3$, $OR_0$ or $COOR_0$ with $R_0$ being H or a linear or branched, $C_1$-$C_{10}$, alkyl radical.

26. The method of claim 13, wherein, when Z=Z'=O, at least one of the $R_2$ and $R_3$ groups represents $CF_3$ or $COOR_0$ with $R_0$ being a saturated, linear or branched, $C_1$-$C_5$, alkyl radical.

27. The method of claim 13, wherein, when Z=Z' and Z and Z' are different from G, at least one of the $R_2$ and $R_3$ groups represents $CF_3$ or $COOR_0$, with $R_0$ being H.

28. The method of claim 1 wherein the compound of formula (I) or a mixture of compounds of formula (I) is used at a concentration ranging from $10^{-2}$ to 2%, with respect to the total weight of the composition.

29. The method of claim 1, wherein the composition further comprises at least one compound selected from the group consisting of antiandrogens, cyclosporins, antimicrobials, antifungals, anti-inflammatories and retinoids.

30. The method of claim 1, wherein the composition further comprises at least one compound selected from the group consisting of aminexil, FP receptor agonists and vasodilators.

31. The method of claim 1, wherein the composition further comprises at least one compound selected from the group consisting of aminexil, minoxidil, latanoprost, butaprost and travoprost.

32. A method of inducing the growth of keratinous fibers, or stimulating the growth of keratinous fibers, or slowing the loss of keratinous fibers in a subject in need of same; said method comprising applying to said subject a composition comprising an effective amount of at least one heterocyclic compound of formula (I) or of one of its salts,

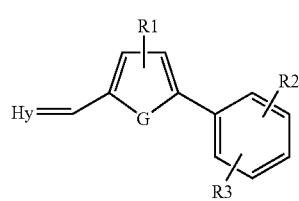

(I)

in which:
Hy represents a heterocycle with of formula (II):

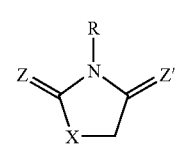

(II)

where Z and Z' independently represent S or O, X independently represents S or O or NH, R denotes a hydrogen, a linear or branched $C_1$-$C_{20}$ alkyl radical or an aryl radical;

G represents O;

$R_1$, $R_2$ and $R_3$ represent, independently of one another, a hydrogen, a halogen, an $OR_0$, $SR_0$, $NR_0R_0'$, $COR_0$, $CSR_0$, $NR_0CONR_0'R_0''$, $C(=NR_0)R_0'$, $C(=NR_0)NR_0'R_0''$, $NR_0C(=NR_0')NR_0''R_0'''$, $OCOR_0$, $COSR_0$, $SCOR_0$, $CSNR_0R_0'$, $NR_0CSR_0'$, $NR_0CSNR_0'R_0''$, $COOR_0$, $CONR_0R_0'$, $CF_3$, $NO_2$, $CN$, $NR_0COR_0'$, $SO_2R_0'$, $SO_2NR_0R_0'$ or $NR_0SO_2R_0'$ group, a saturated linear or branched $C_1$-$C_{20}$ alkyl radical, an unsaturated linear or branched $C_1$-$C_{20}$ alkyl radical, or at least one saturated or unsaturated ring of 4 to 7 atoms, wherein the rings are separate or fused, where $R_0$, $R_0'$, $R_0''$ and $R_0'''$, which are identical or different, denote a hydrogen, a linear or branched $C_1$-$C_{20}$ alkyl radical or an aryl radical.

33. The method of claim 32, wherein the keratinous fibers are the hair, eyebrows, eyelashes, beard hairs, moustache hairs and pubic hairs.

34. The method of claim 32, wherein the keratinous fibers are the hair.

35. The method of claim 32, wherein the application of the composition is topical.

36. The method of claim 34, wherein the heterocyclic compound of formula (I) exhibits the following formula (IIIa) or the corresponding salt form:

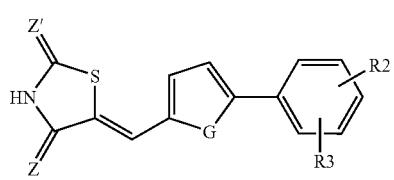

(IIIa)

in which Z and Z' independently represent O or S and G represents O; and at least one of the $R_2$ and $R_3$ groups represents $CF_3$, $OR_0$ or $COOR_0$ with $R_0$ being H or a linear or branched, $C_1$-$C_{10}$, alkyl radical.

37. The method of claim 34, wherein the heterocyclic compound of formula (I) is selected from the group consisting of:

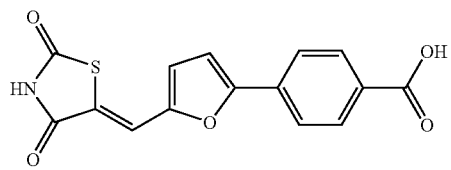

-continued

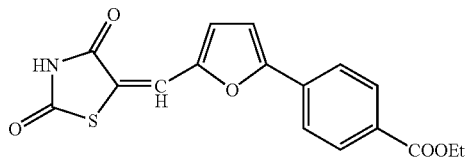

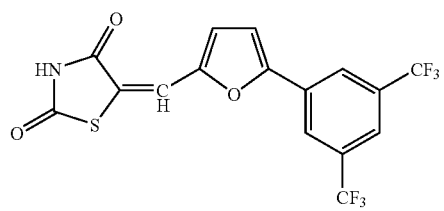

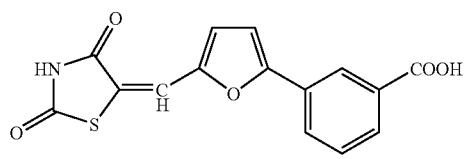

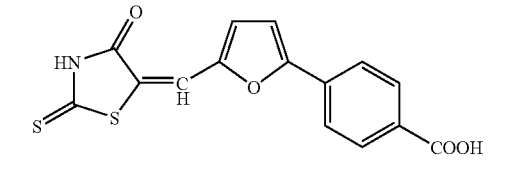

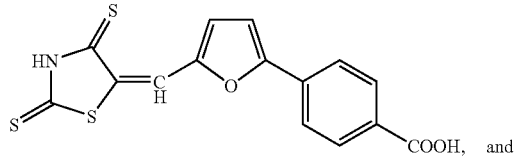

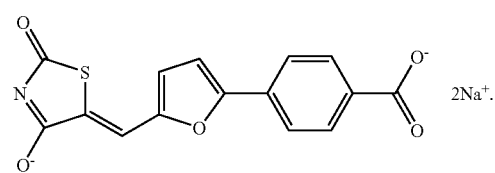

38. The method of claim 34, wherein the heterocyclic compound of formula (I) is:

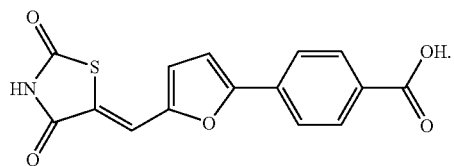

39. A method of inducing the growth of keratinous fibers, or stimulating the growth of keratinous fibers, or slowing the loss of keratinous fibers or increasing the density of keratinous fibers in a subject in need of same; said method comprising applying to said subject a composition comprising an effective amount of at least one heterocyclic compound of the formula:

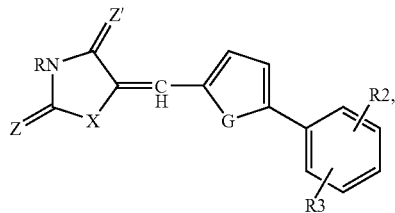

or of one of its salts, in which:

Z and Z' independently represent S or O,

X independently represents S or O or NH,

R denotes a hydrogen or a linear or branched $C_1$-$C_{10}$ alkyl radical;

G represents O or S;

$R_2$ and $R_3$ represent, independently of each other, a hydrogen, CN, $NO_2$, $CF_3$, phenyl, an $OR_0$, a $COOR_0$ radical, a saturated linear or branched $C_1$-$C_{20}$ alkyl radical optionally substituted by $OR_0$, where $R_0$ denotes a hydrogen or a linear or branched $C_1$-$C_{20}$ alkyl radical.

40. The method of claim 39, wherein at least one of $R_2$ and $R_3$ represent, independently of each other, a hydrogen, CN, $NO_2$, $CF_3$, phenyl, an $OR_0$, a $COOR_0$ radical, a saturated linear or branched $C_1$-$C_{10}$ alkyl radical optionally substituted by $OR_0$, where $R_0$ denotes a hydrogen, or a linear or branched $C_1$-$C_{20}$ alkyl radical.

41. The method of claim 39, wherein at least one of $R_2$ and $R_3$ represent, independently of each other, a hydrogen, CN, $NO_2$, $CF_3$, phenyl, an $OR_0$, a $COOR_0$ radical, a saturated linear or branched $C_1$-$C_{10}$ alkyl radical optionally substituted by $OR_0$, where $R_0$ denotes a hydrogen or a linear or branched $C_1$-$C_{10}$ alkyl radical.

42. A method of caring for human keratinous fibers, or inducing and/or stimulating the growth of human keratinous fibers, or slowing the loss of human keratinous fibers and/or increasing the density of human keratinous fibers and/or treating androgenic alopecia in a subject in need of same; said method comprising applying to said subject a composition comprising an effective amount of at least one heterocyclic compound of the formula:

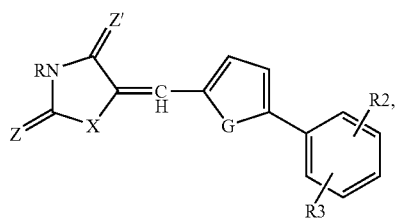

or of one of its salts, in which:

Z and Z' independently represent S or O,

X independently represents S or O or NH,

R denotes a hydrogen or a linear or branched $C_1$-$C_{10}$ alkyl radical;

G represents O or S;

$R_2$ and $R_3$ represent, independently of each other, a hydrogen, CN, $NO_2$, $CF_3$, phenyl, an $OR_0$, a $COOR_0$ radical, a saturated linear or branched $C_1$-$C_{20}$ alkyl radical optionally substituted by $OR_0$, where $R_0$ denotes a hydrogen or a linear or branched $C_1$-$C_{20}$ alkyl radical.

43. The method of claim 42, wherein at least one of $R_2$ and $R_3$ represent, independently of each other, a hydrogen, CN, $NO_2$, $CF_3$, phenyl, an $OR_0$, a $COOR_0$ radical, a saturated linear or branched $C_1$-$C_{10}$ alkyl radical optionally substituted by $OR_0$, where $R_0$ denotes a hydrogen, a linear or branched $C_1$-$C_{20}$ alkyl radical.

44. The method of claim 42, wherein at least one of $R_2$ and $R_3$ represent, independently of each other, a hydrogen, CN, $NO_2$, $CF_3$, phenyl, an $OR_0$, a $COOR_0$ radical, a saturated linear or branched $C_1C_{10}$ alkyl radical optionally substituted by $OR_0$, where $R_0$ denotes a hydrogen or a linear or branched $C_1$-$C_{10}$ alkyl radical.

45. A method of inhibiting 15-hydroxyprostaglandin dehydrogenase and thus maintaining and/or increasing the density of human keratinous fibers in a subject in need of same, said method comprising applying to said subject a composition comprising an effective amount of at least one heterocyclic compound of the formula:

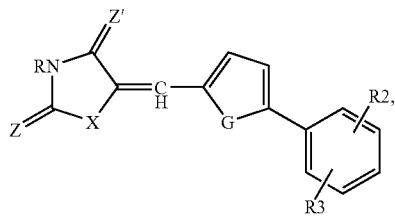

or of one of its salts, in which:

Z and Z' independently represent S or O,

X independently represents S or O or NH,

R denotes a hydrogen or a linear or branched $C_1$-$C_{10}$ alkyl radical;

G represents O or S;

$R_2$ and $R_3$ represent, independently of each other, a hydrogen, CN, $NO_2$, $CF_3$, phenyl, an $OR_0$, a $COOR_0$ radical, a saturated linear or branched $C_1$-$C_{20}$ alkyl radical optionally substituted by $OR_0$, where $R_0$ denotes a hydrogen or a linear or branched $C_1$-$C_{20}$ alkyl radical.

46. The method of claim 45, wherein at least one of $R_2$ and $R_3$ represent, independently of each other, a hydrogen, CN, $NO_2$, $CF_3$, phenyl, an $OR_0$, a $COOR_0$ radical, a saturated linear or branched $C_1$-$C_{20}$ alkyl radical optionally substituted by $OR_0$, where $R_0$ denotes a hydrogen, a linear or branched $C_1$-$C_{20}$ alkyl radical.

47. The method of claim 45, wherein at least one of $R_2$ and $R_3$ represent, independently of each other, a hydrogen, CN, $NO_2$, $CF_3$, phenyl, an $OR_0$, a $COOR_0$ radical, a saturated linear or branched $C_1$-$C_{10}$ alkyl radical optionally substituted by $OR_0$, where $R_0$ denotes a hydrogen or a linear or branched $C_1$-$C_{10}$ alkyl radical.

48. A method of reducing hair loss and/or increasing hair density and/or treating androchronogenetic alopecia and/or treating alopecia of natural origin in a subject in need of same; said method comprising applying to said subject a cosmetic or pharmaceutical composition comprising an effective amount of at least one heterocyclic compound of the formula:

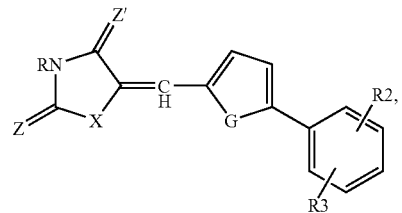

or of one of its salts, in which:

Z and Z' independently represent S or O,

X independently represents S or O or NH,

R denotes a hydrogen or a linear or branched $C_1$-$C_{10}$ alkyl radical;

G represents O or S;

$R_2$ and $R_3$ represent, independently of each other, a hydrogen, CN, $NO_2$, $CF_3$, phenyl, an $OR_0$, a $COOR_0$ radical, a saturated linear or branched $C_1$-$C_{20}$ alkyl radical optionally substituted by $OR_0$, where $R_0$ denotes a hydrogen or a linear or branched $C_1$-$C_{20}$ alkyl radical.

49. The method of claim 48, wherein at least one of $R_2$ and $R_3$ represent, independently of each other, a hydrogen, CN, $NO_2$, $CF_3$, phenyl, an $OR_0$, a $COOR_0$ radical, a saturated linear or branched $C_1$-$C_{10}$ alkyl radical optionally substituted by $OR_0$, where $R_0$ denotes a hydrogen, a linear or branched $C_1$-$C_{20}$ alkyl radical.

50. The method of claim 48, wherein at least one of $R_2$ and $R_3$ represent, independently of each other, a hydrogen, CN, $NO_2$, $CF_3$, phenyl, an $OR_0$, a $COOR_0$ radical, a saturated linear or branched $C_1$-$C_{10}$ alkyl radical optionally substituted by $OR_0$, where $R_0$ denotes a hydrogen or a linear or branched $C_1$-$C_{10}$ alkyl radical.

51. A method of inducing and/or stimulating the growth of eyelashes and/or increasing the density of eyelashes in a subject in need of same; said method comprising applying to said subject a cosmetic composition comprising an effective amount at least one heterocyclic compound of the formula:

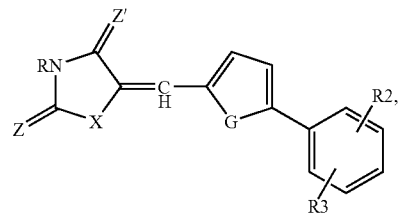

or of one of its salts, in which:

Z and Z' independently represent S or O,

X independently represents S or O or NH,

R denotes a hydrogen or a linear or branched $C_1$-$C_{10}$ alkyl radical;

G represents O or S;

$R_2$ and $R_3$ represent, independently of each other, a hydrogen, CN, $NO_2$, $CF_3$, phenyl, an $OR_0$, a $COOR_0$ radical, a saturated linear or branched $C_1$-$C_{20}$ alkyl radical optionally substituted by $OR_0$, where $R_0$ denotes a hydrogen or a linear or branched $C_1$-$C_{20}$ alkyl radical.

52. The method of claim 51, wherein at least one of $R_2$ and $R_3$ represent, independently of each other, a hydrogen, CN, $NO_2$, $CF_3$, phenyl, an $OR_0$, a $COOR_0$ radical, a saturated linear or branched $C_1$-$C_{10}$ alkyl radical optionally substituted by $OR_0$, where $R_0$ denotes a hydrogen, a linear or branched $C_1$-$C_{20}$ alkyl radical.

53. The method of claim 51, wherein at least one of $R_2$ and $R_3$ represent, independently of each other, a hydrogen, CN, $NO_2$, $CF_3$, phenyl, an $OR_0$, a $COOR_0$ radical, a saturated linear or branched $C_1$-$C_{10}$ alkyl radical optionally substituted by $OR_0$, where $R_0$ denotes a hydrogen or a linear or branched $C_1$-$C_{20}$ alkyl radical.

54. A method for improving the condition and/or appearance of human eyelashes in a subject in need of same, said method comprising applying to the eyelashes and/or eyelids of said subject a mascara composition comprising at least one compound of the formula:

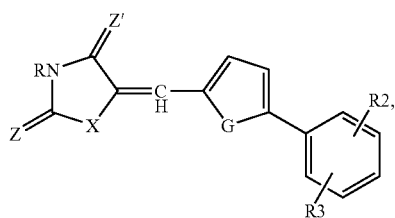

or of one of its salts, in which:

Z and Z' independently represent S or O,

X independently represents S or O or NH,

R denotes a hydrogen or a linear or branched $C_1$-$C_{10}$ alkyl radical;

G represents O or S;

$R_2$ and $R_3$ represent, independently of each other, a hydrogen, CN, $NO_2$, $CF_3$, phenyl, an $OR_0$, a $COOR_0$ radical, a saturated linear or branched $C_1$-$C_{20}$ alkyl radical optionally substituted by $OR_0$, where $R_0$ denotes a hydrogen or a linear or branched $C_1$-$C_{20}$ alkyl radical, and leaving this composition in contact with the eyelashes and/or eyelids.

55. The method of claim 54, wherein at least one of $R_2$ and $R_3$ represent, independently of each other, a hydrogen, CN, $NO_2$, $CF_3$, phenyl, an $OR_0$, a $COOR_0$ radical, a saturated linear or branched $C_1$-$C_{10}$ alkyl radical optionally substituted by $OR_0$, where $R_0$ denotes a hydrogen, a linear or branched $C_1$-$C_{20}$ alkyl radical.

56. The method of claim 54, wherein at least one of $R_2$ and $R_3$ represent, independently of each other, a hydrogen, CN, $NO_2$, $CF_3$, phenyl, an $OR_0$, a $COOR_0$ radical, a saturated linear or branched $C_1$-$C_{10}$ alkyl radical optionally substituted by $OR_0$, where $R_0$ denotes a hydrogen or a linear or branched $C_1$-$C_{10}$ alkyl radical.

57. A method for improving the condition and/or appearance of human scalp in a subject in need of same, said method comprising applying to the hair and/or the scalp of said subject a cosmetic composition comprising an effective amount of at least one compound of the formula:

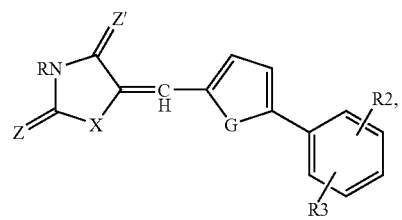

or of one of its salts, in which:

Z and Z' independently represent S or O,

X independently represents S or O or NH,

R denotes a hydrogen or a linear or branched $C_1$-$C_{10}$ alkyl radical;

G represents O or S;

$R_2$ and $R_3$ represent, independently of each other, a hydrogen, CN, $NO_2$, $CF_3$, phenyl, an $OR_0$, a $COOR_0$ radical, a saturated linear or branched $C_1$-$C_{20}$ alkyl radical optionally substituted by $OR_0$, where $R_0$ denotes a hydrogen or a linear or branched $C_1$-$C_{20}$ alkyl radical, and leaving this composition in contact with the hair and/or the scalp and optionally rinsing the hair and/or the scalp.

58. The method of claim 57, wherein at least one of $R_2$ and $R_3$ represent, independently of each other, a hydrogen, CN, $NO_2$, $CF_3$, phenyl, an $OR_0$, a $COOR_0$ radical, a saturated linear or branched $C_1$-$C_{10}$ alkyl radical optionally substituted by $OR_0$, where $R_0$ denotes a hydrogen or a linear or branched $C_1$-$C_{20}$ alkyl radical.

59. The method of claim 57, wherein at least one of $R_2$ and $R_3$ represent, independently of each other, a hydrogen, CN, $NO_2$, $CF_3$, phenyl, an $OR_0$, a $COOR_0$ radical, a saturated linear or branched $C_1$-$C_{10}$ alkyl radical optionally substituted by $OR_0$, where $R_0$ denotes a hydrogen or a linear or branched $C_1$-$C_{10}$ alkyl radical.

60. A method of preserving the amount and/or the activity of prostaglandins in the hair follicle in a subject in need of same, said method comprising applying to the skin and/or hair of said subject a cosmetic composition comprising an effective amount of at least one heterocyclic compound of the formula:

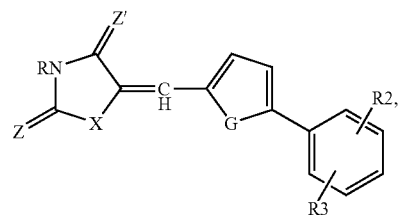

or of one of its salts, in which:

Z and Z' independently represent S or O,

X independently represents S or O or NH,

R denotes a hydrogen or a linear or branched $C_1$-$C_{10}$ alkyl radical;

G represents O or S;

R₂ and R₃ represent, independently of each other, a hydrogen, CN, NO₂, CF₃, phenyl, an OR₀, a COOR₀ radical, a saturated linear or branched C₁-C₂₀ alkyl radical optionally substituted by OR₀, where R₀ denotes a hydrogen or a linear or branched C₁-C₂₀ alkyl radical.

61. The method of claim 60, wherein at least one of R₂ and R₃ represent, independently of each other, a hydrogen, CN, NO₂, CF₃, phenyl, an OR₀, a COOR₀ radical, a saturated linear or branched C₁-C₁₀ alkyl radical optionally substituted by OR₀, where R₀ denotes a hydrogen or a linear or branched C₁-C₂₀ alkyl radical.

62. The method of claim 60, wherein at least one of R₂ and R₃ represent, independently of each other, a hydrogen, CN, NO₂, CF₃, phenyl, an OR₀, a COOR₀ radical, a saturated linear or branched C₁-C₁₀ alkyl radical optionally substituted by OR₀, where R₀ denotes a hydrogen or a linear or branched C₁-C₁₀ alkyl radical.

63. A method of inducing the growth of keratinous fibers, or stimulating the growth of keratinous fibers, or slowing the loss of keratinous fibers in a subject in need of same; said method comprising applying to said subject a composition comprising an effective amount of at least one heterocyclic compound of the formula:

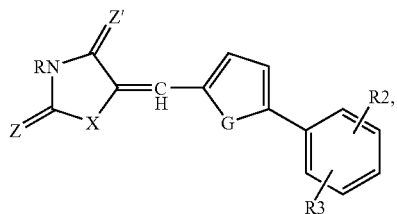

or of one of its salts, in which:

Z and Z' independently represent S or O,

X independently represents S or O or NH,

R denotes a hydrogen or a linear or branched C₁-C₁₀ alkyl radical;

G represents O or S;

R₂ and R₃ represent, independently of each other, a hydrogen, CN, NO₂, CF₃, phenyl, an OR₀, a COOR₀ radical, a saturated linear or branched C₁-C₂₀ alkyl radical optionally substituted by OR₀, where R₀ denotes a hydrogen or a linear or branched C₁-C₂₀ alkyl radical.

64. The method of claim 63, wherein at least one of R₂ and R₃ represent, independently of each other, a hydrogen, CN, NO₂, CF₃, phenyl, an OR₀, a COOR₀ radical, a saturated linear or branched C₁-C₁₀ alkyl radical optionally substituted by OR₀, where R₀ denotes a hydrogen or a linear or branched C₁-C₂₀ alkyl radical.

65. The method of claim 63, wherein at least one of R₂ and R₃ represent, independently of each other, a hydrogen, CN, NO₂, CF₃, phenyl, an OR₀, a COOR₀ radical, a saturated linear or branched C₁-C₁₀ alkyl radical optionally substituted by OR₀, where R₀ denotes a hydrogen or a linear or branched C₁-C₁₀ alkyl radical.

66. The method of claim 3 wherein the heterocyclic compound of formula (I) exhibits the following formula (IIIa) or the corresponding salt form:

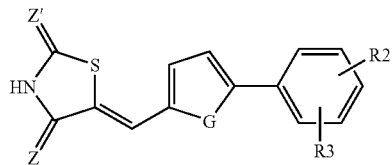

in which Z, Z' and G independently represent O or S; and at least one of the R₂ and R₃ groups represents CF₃, OR₀ or COOR₀ with R₀ being H or a saturated or unsaturated, linear or branched, C₁-C₂₀ alkyl radical.

67. The method of claim 3, wherein the compound of formula (I) is selected from the group consisting of:

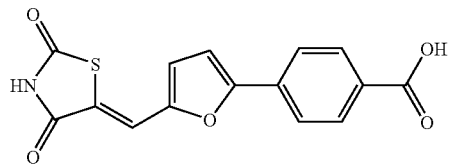

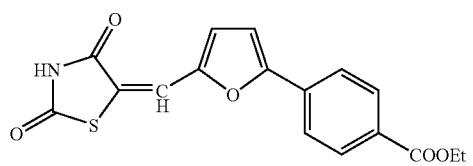

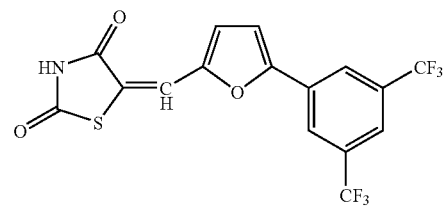

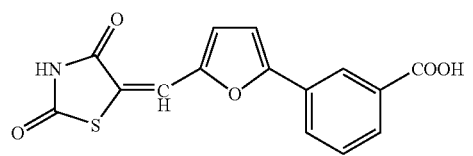

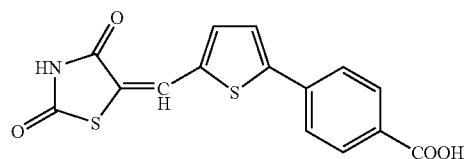

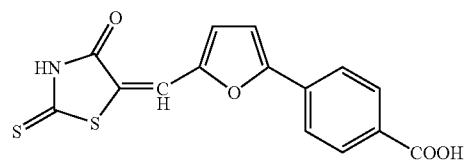

-continued
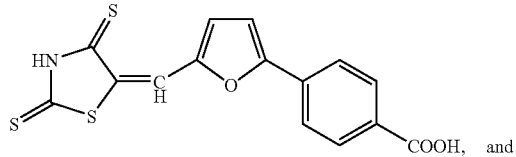 COOH, and
-continued
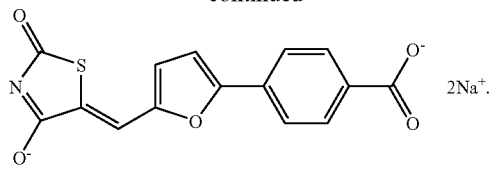 2Na+.
* * * * *